(12) United States Patent
Kao et al.

(10) Patent No.: US 11,622,960 B2
(45) Date of Patent: Apr. 11, 2023

(54) MICROTUBULE POLYMERIZATION INHIBITOR PRODRUGS AND METHODS OF USING THE SAME

(71) Applicant: UNIVERSITY OF MARYLAND, BALTIMORE, Baltimore, MD (US)

(72) Inventors: Joseph Pao Yung Kao, Silver Spring, MD (US); Christopher William Ward, Baltimore, MD (US); Ramzi Khairallah, New Market, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/624,787

(22) PCT Filed: Jun. 19, 2018

(86) PCT No.: PCT/US2018/038300
§ 371 (c)(1),
(2) Date: Dec. 19, 2019

(87) PCT Pub. No.: WO2018/236879
PCT Pub. Date: Dec. 27, 2018

(65) Prior Publication Data
US 2020/0215035 A1  Jul. 9, 2020

Related U.S. Application Data

(60) Provisional application No. 62/521,749, filed on Jun. 19, 2017, provisional application No. 62/521,731, filed on Jun. 19, 2017.

(51) Int. Cl.
| | |
|---|---|
| *A61K 31/4184* | (2006.01) |
| *A61P 21/00* | (2006.01) |
| *A61K 31/135* | (2006.01) |
| *A61K 31/165* | (2006.01) |
| *A61K 45/06* | (2006.01) |

(52) U.S. Cl.
CPC ........ *A61K 31/4184* (2013.01); *A61K 31/135* (2013.01); *A61K 31/165* (2013.01); *A61K 45/06* (2013.01); *A61P 21/00* (2018.01)

(58) Field of Classification Search
CPC .............. A61K 31/4184; A61K 31/135; A61K 31/165
See application file for complete search history.

(56) References Cited

U.S. PATENT DOCUMENTS

| | | | |
|---|---|---|---|
| 5,684,018 A | 11/1997 | Alexander | |
| 9,458,101 B2 * | 10/2016 | Tuszynski | G01N 33/5088 |
| 2004/0204370 A1 | 10/2004 | Yang | |
| 2013/0011417 A1 | 1/2013 | Han et al. | |
| 2014/0256644 A1 | 9/2014 | Ward et al. | |
| 2014/0294851 A1 | 10/2014 | Nguyen | |

FOREIGN PATENT DOCUMENTS

| | | |
|---|---|---|
| EP | 3641741 A | 4/2020 |
| WO | 2018/236879 A1 | 12/2018 |

OTHER PUBLICATIONS

International Search Report dated Oct. 30, 2018 for International Application No. PCT/US2018/038300.
Partial Supplementary European Search Report dated Feb. 5, 2021 for EP Application No. 18819941.8.
Muzaffar et al., "Antitubulin effects of derivatives of 3-demethylthiocolchicine, methylthioesters of natural colchicinoids and thioketones derived from thiocolchicine" Journal of Medicinal Chemistry, American Chemical Society, US,vol. 33. No. 2 (1990).
Leung et al., "Colchicine-Update on mechanisms of action and therapeutic uses" Seminars in Arthritis and Rheumatism, vol. 45, No. 3 (2015).
European Extended Search Report dated May 7, 2021 for EP Application No. 18819941.8.
Alexander et al. (Acyloxy)alkyl carbamate prodrugs of norfloxacin', J Med Chem. (1991) vol. 34(1), pp. 78-81. abstract; p. 79, col. 1, pare 3.
Extended European Search and Exam Report dated Jan. 27, 2022 for EP Application No. 18819941.8.
Crielaard et al., Liposomes as carriers for colchicine-derived prodrugs: Vascular disrupting nanomedicines with tailorable drug release kinetics. European Journal of Pharmaceutical Sciences, 45 (2012).
Allen, D.G. et al. Absence of Dystrophin Disrupts Skeletal Muscle Signaling: Roles of Ca2+, Reactive Oxygen Species, and Nitric Oxide in the Development of Muscular Dystrophy. Physiol Rev. 2016, 96(1), 253-305.
Yang LP. Oral colchicine (colcrys®) in the treatment and prophylaxis of gout: profile report. Drugs Aging. 2010, 27(10), 855-857.
Cocco, G., Chu, D. C., Pandolfi, S. Colchicine in clinical medicine. A guide for internists. Eur J Intern Med., 2010, 21 (6), 503-508.
Cohn RD, et al. Angiotensin II type 1 receptor blockade attenuates TGF-beta-induced failure of muscle regeneration in multiple myopathic states. Nat Med. 2007, 13(2), 204-10.
Deftereos S, et al. Colchicine and the heart: pushing the envelope J Am Coll Cardiol. 2013, 62(20), 1817-1825.
Dorsey SG, et al. Genetic deletion of trkB.TI increases neuromuscular function. Am J Physiol Cell Physiol. 2012, 302 (1), C141-C153.
Ferron GM, et al. Oral absorption characteristics and pharmacokinetics of colchicine in healthy volunteers after single and multiple doses. J Clin Pharmacol 1996, 36(10), 874-883.
Goyenvalle A, et al. Therapeutic approaches to muscular dystrophy. Hum Mol Genet. 2011, 20(R1), R69-R78.
Kendall GC, et al. Dantrolene enhances antisense-mediated exon skipping in human and mouse models of Duchenne muscular dystrophy. Sci Transl Med. 2012, 4(164), 164ra160.
Kerr, J., Robison, P., Shi, G et al. Detyrosinated microtubules modulate mechanotransduction in heart and skeletal muscle. Nat Commun. 2015, 6, 8526.
Khairallah RJ, et al. Microtubules underlie dysfunction in duchenne muscular dystrophy. Sci Signal. 2012, 5(236), ra56.

(Continued)

*Primary Examiner* — Kevin E Weddington
(74) *Attorney, Agent, or Firm* — Morgan, Lewis & Bockius LLP

(57) ABSTRACT

Prodrugs of colchicine, de-acetyl colchicine, colcemid, and nocodazole are provided as therapies for the treatment of diseases ameliorated by the inhibition of microtubule polymerization.

9 Claims, 22 Drawing Sheets

(56) References Cited

OTHER PUBLICATIONS

Lim KR, Maruyama R, Yokota T. Eteplirsen in the treatment of Duchenne muscular dystrophy. Drug Des Devel Ther. 2017, 11, 533-545.
Lovering RM, et al. Malformed mdx myofibers have normal cytoskeletal architecture yet altered EC coupling and stress-induced Ca2+ signaling. Am J Physiol Cell Physiol. 2009, 297(3), C571-C580.
Niel E, Scherrmann JM. Colchicine today. Joint Bone Spine. 2006, 73(6), 672-678.
Pratt SJP, et al. Effects of in vivo injury on the neuromuscular junction in healthy and dystrophic muscles. J Physiol. 2013, 591(2), 559-750.
Prosser BL, et al. X-ROS signaling in the heart and skeletal muscle stretch-dependent local ROS regulates [Ca2+]i. J Mol Cell Cardiol. 2013, 58, 172-181.
Sozeri B, Kasapcopur O. Biological agents in familial Mediterranean fever focusing on colchicine resistance and amyloidosis. Curr Med Chem. 2015, 22(16), 1986-1991.
Tidball, J., Wehling-Henricks, M. Evolving Therapeutic Strategies for Duchenne Muscular Dystrophy: Targeting Downstream Events. Pediatr Res. 2004, 56(6), 831-841.

\* cited by examiner

MICROTUBULE POLYMERIZATION INHIBITOR PRODRUGS AND METHODS OF USING THE SAME

CROSS-REFERENCE TO RELATED APPLICATIONS

This application is a U.S. National Stage Entry of International Patent Application Serial No. PCT/US2018/038300, filed on Jun. 19, 2018, which in turn claims the benefit of U.S. Provisional Patent Applications Nos. 62/521,731, filed Jun. 19, 2017, and 62/521,749, filed Jun. 19, 2017, each of which is incorporated by reference herein in its entirety.

FIELD OF THE INVENTION

The invention described herein relates generally to prodrug analogs of compounds that inhibit microtubule polymerization and methods of using the same and more particularly, but not exclusively, to prodrug analogs of colchicine, colcemid, and nocodazole.

BACKGROUND OF THE INVENTION

A number of diseases may be treated by inhibitors of microtubule polymerization, such as colchicine, de-acetyl colchicine, colcemid, and nocodazole. However, while these drugs may be the standard of care for certain diseases, such as inflammatory gout and Familial Mediterranean Fever (FMF) in the case of colchicine, their pharmacokinetic profiles are not ideal for chronic use.

Accordingly, there is a need in the field for prodrug analogs of such inhibitors of microtubule polymerization with improved pharmacokinetic profiles that allow for greater dosing regimen variability and expanded treatment options.

SUMMARY OF THE INVENTION

In an embodiment, prodrug compounds are described herein that, upon metabolism, result in active inhibitors of microtubule polymerization. In some embodiments, the prodrug compounds described herein result in the active-metabolites: colchicine, de-acetyl colchicine, colcemid, and nocodazole.

In an embodiment, the invention includes a prodrug of formula (I), formula (II), formula (III), formula (IV), or formula (V):

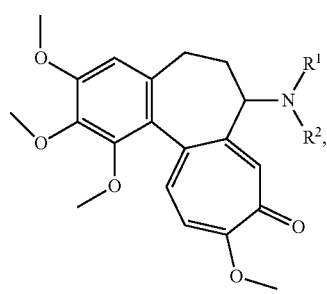

(I)

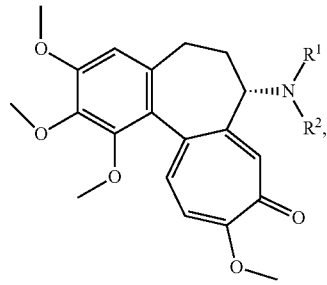

(II)

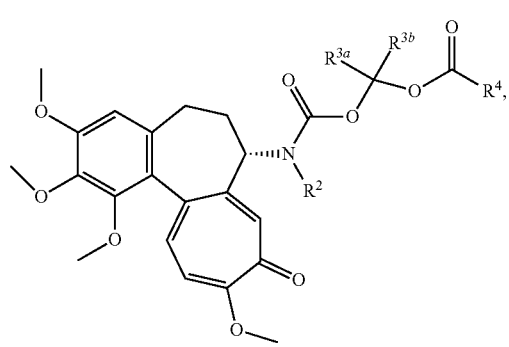

(III)

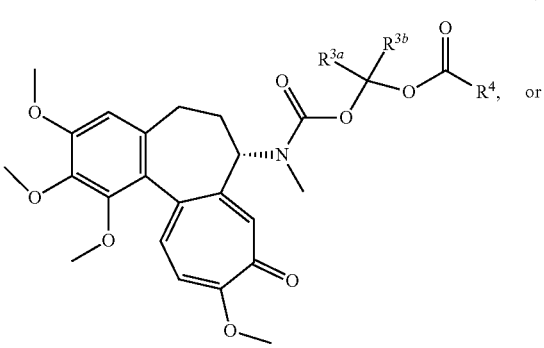

(IV)

or

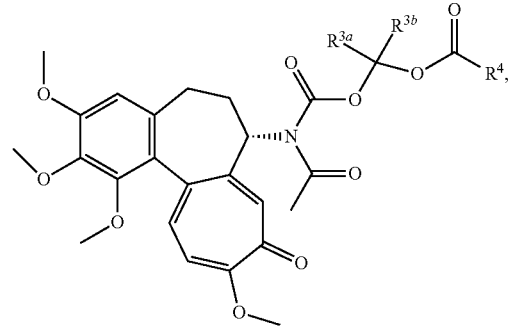

(V)

wherein $R^1$ may be a substituent selected from the group consisting of carboxyl, and optionally substituted ester, and —C(=O)O-alkyl-OC(=O)-alkyl;

$R^2$ may be a substituent selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

$R^{3a}$ and $R^{3b}$ may be substituents independently selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

$R^4$ may be a substituent selected from the group consisting of H, and optionally substituted alkyl, alkoxy, -(alkoxy)$_n$-alkyl, heteroalkyl, and -(alkyl)$_n$-alkyl; n is an integer of 1-250; and the pharmaceutically acceptable salts thereof.

In some embodiments, the prodrug of any one of formula (I), formula (II), formula (III), formula (IV), or formula (V), wherein the active-metabolite of the prodrug may be colchicine, de-acetyl colchicine, or colcemid.

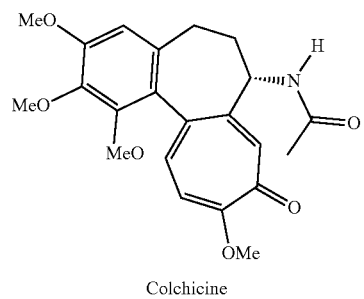

Colchicine

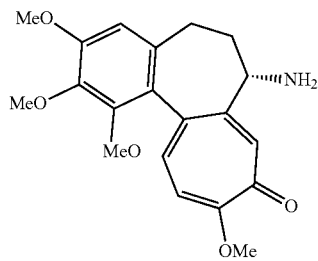

De-axetyl Colchicine

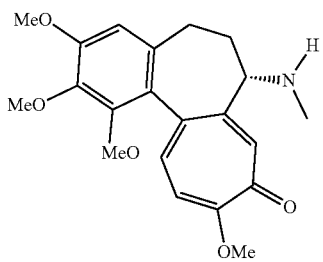

Colcemid

In an embodiment, the invention includes a prodrug of formula (VI), formula (VII), formula (VIII), formula (IX), or formula (X):

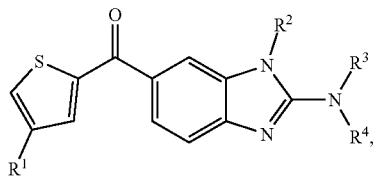

(VI)

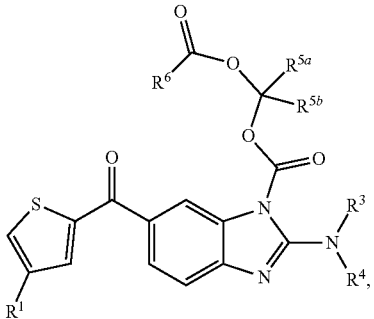

(VII)

(VIII)

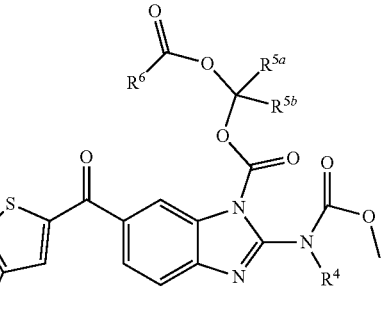

(IX)

(X)

wherein $R^1$ may be a substituent selected from the group consisting of H, and optionally substituted alkyl, -alkyl-CN, alkyl-ester, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

R² may be a substituent selected from the group consisting of H, and optionally substituted alkyl, carboxyl, ester, and —C(=O)O-alkyl-OC(=O)-alkyl;

R³ may be a substituent selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

R⁴ may be a substituent selected from the group consisting of H, and optionally substituted alkyl, carboxyl, ester, and —C(=O)O-alkyl-OC(=O)-alkyl;

$R^{5a}$ and $R^{5b}$ may be substituents independently selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

R⁶ may be a substituent selected from the group consisting of H, and optionally substituted alkyl, alkoxy, -(alkoxy)$_n$-alkyl, heteroalkyl, and -(alkyl)$_n$-alkyl; n is an integer of 1-250; and the pharmaceutically acceptable salts thereof.

In some embodiments, the active metabolite of formula (VI), formula (VII), formula (VIII), formula (IX), or formula (X) may be nocodazole.

Nocodazole

In some embodiments, the active-metabolites of the prodrugs described herein inhibit microtubule polymerization.

In an embodiment, the invention includes a pharmaceutical composition for treating a disease ameliorated by the inhibition of microtubule polymerization. In some embodiments, the disease may be selected from the group consisting of Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF). In some embodiments, the pharmaceutical composition described herein may include a therapeutically effective amount of a prodrug of formula (I), formula (II), formula (III), formula (IV), formula (V), formula (VI), formula (VII), formula (VIII), formula (IX), or formula (X), or a pharmaceutically acceptable salt thereof, and a pharmaceutically acceptable carrier.

In some embodiments, the pharmaceutical compositions of the invention may include a therapeutically effective amount of an additional pharmaceutical ingredient selected from the group consisting of a non-glucocorticosteroid, a compound that increases utrophin expression, eteplirsen, 5-(ethylsulfonyl)-2-(naphthalen-2-yl)benzo[d]oxazole, prednisone, deflazacort, and a combination thereof.

In an embodiment, the invention includes a method of treating a disease ameliorated by the inhibition of microtubule polymerization. In some embodiments, the disease may be selected from the group consisting of Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF). In some embodiments, the method may include the step of administering a therapeutically effective amount of a prodrug of formula (I), formula (II), formula (III), formula (IV), formula (V), formula (VI), formula (VII), formula (VIII), formula (IX), or formula (X), or a pharmaceutically salt thereof, and a pharmaceutically acceptable carrier.

In some embodiments, the methods of the invention may include the step of administering a therapeutically effective amount of an additional pharmaceutical ingredient selected from the group consisting of a non-glucocorticosteroid, a compound that increases utrophin expression, eteplirsen, 5-(ethylsulfonyl)-2-(naphthalen-2-yl)benzo[d]oxazole, prednisone, deflazacort, and a combination thereof.

BRIEF DESCRIPTION OF THE DRAWINGS

The foregoing summary, as well as the following detailed description of the invention, will be better understood when read in conjunction with the appended drawings.

FIG. 2D).

FIG. 6G: aggregate results for control, 1 µM, 10 µM, and 100 µM colchicine at 10 minutes, 20 minutes, and 30 minutes).

FIG. 7G: aggregate results for 0.3 µM, 1 µM, 3 µM, and 10 µM deacetyl-colchicine at 10 minutes, 20 minutes, 30 minutes, 45 minutes, 60 minutes, and 90 minutes).

FIG. 8G: aggregate results for 0.3 µM, 1 µM, 10 µM, and 100 µM compound 7 at 10 minutes, 20 minutes, 30 minutes, 60 minutes, 90 minutes, and 120 minutes).

FIG. 9G: aggregate results for 1 µM, 10 µM, and 100 µM compound 8 at 10 minutes, 20 minutes, 30 minutes, 60 minutes, 90 minutes, and 120 minutes).

FIG. 10G: aggregate results for 1 µM, 10 µM, and 100 µM compound 9 at 10 minutes, 20 minutes, 30 minutes, 60 minutes, 90 minutes, and 120 minutes).

FIG. 11G: aggregate results for 1 µM, 10 µM, and 100 µM compound 10 at 10 minutes, 20 minutes, 30 minutes, 60 minutes, 90 minutes, and 120 minutes).

DETAILED DESCRIPTION OF THE INVENTION

Figure 1B:
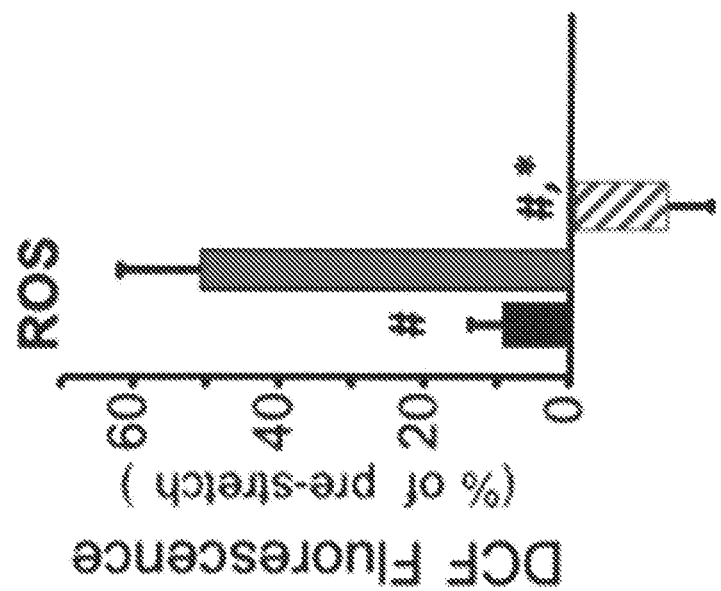
FIGS. 1A-1E illustrate that microtubules underlie dysfunction in DMD. Aggregate DFF signals from WT (Black; n=5) and mdx (Red; n=6) muscle fibers (FIG. 1A). Mean values from A show a significant increase in X-ROS in the mdx (*p<0.05) that is blunted by colchicine (FIG. 1B). X-ROS leads to Ca²⁺ influx that is blocked by microtubule depolymerization (FIG. 1C). Microtubule density is elevated in mdx fibers and reduced by colchicine (FIGS. 1D and 1E).
Figure 1A:
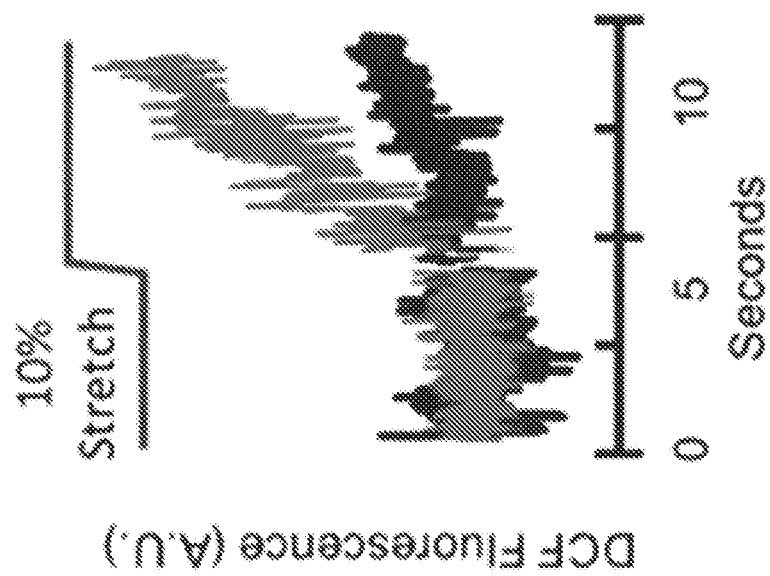
Figure 1C:
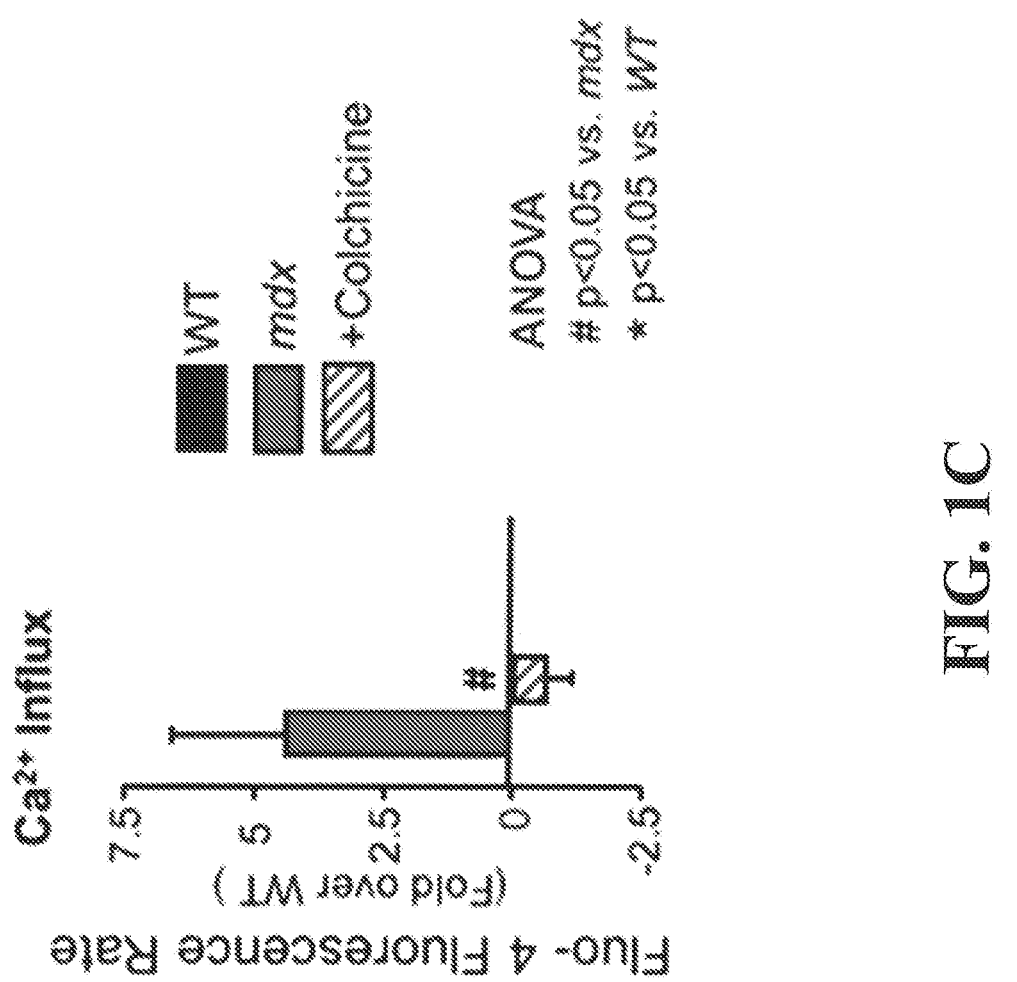
Figure 1D:
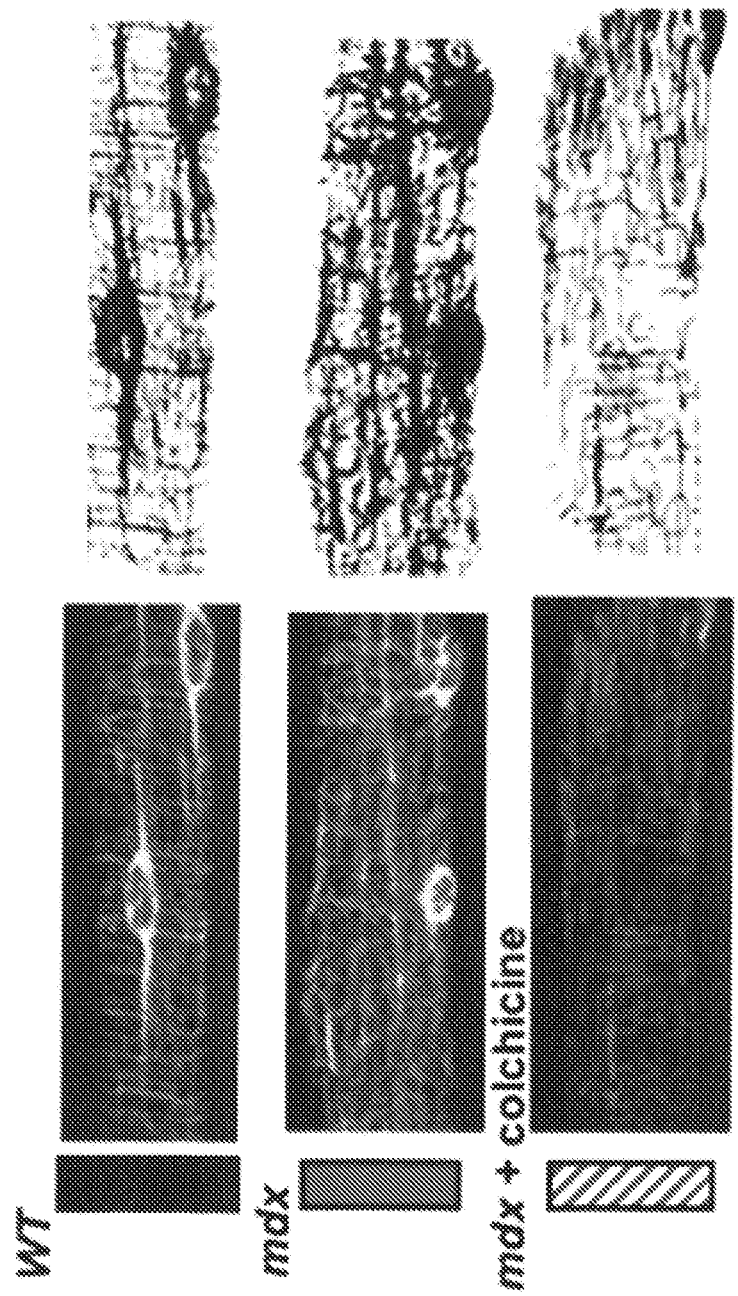
Figure 1E:
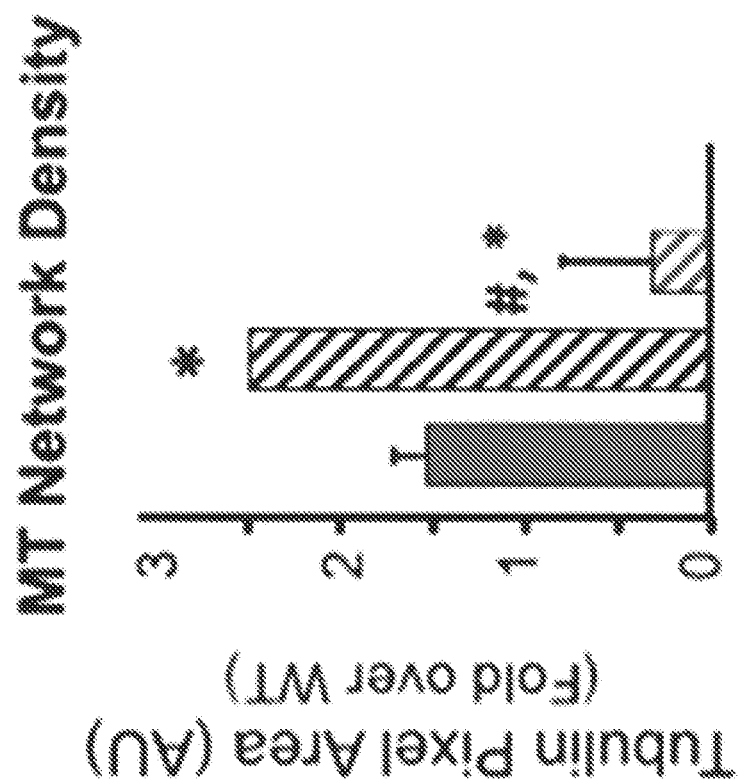
Figure 2B:
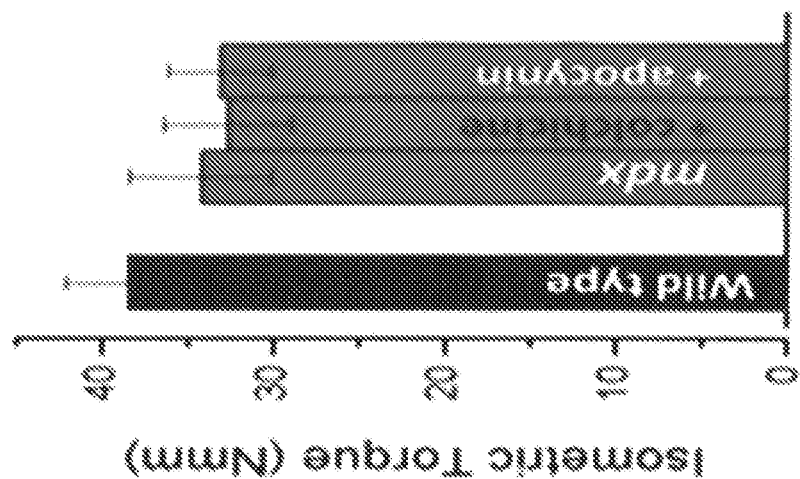
FIGS. 2A-2D illustrate that targeting microtubule density in vivo is solely sufficient to decrease contraction-induced injury in mdx mice. Nerve evoked torque and eccentric injury of the gastrocnemius muscle in vivo (FIG. 2A). Adult mdx mice (~5 months) treated in vivo with either colchicine or apocynin produce similar tetanic isometric torque as vehicle treated mdx (FIG. 2B). Normalized torque records of the initial (time=0; wild-type in black, mdx in red) and 20$^{th}$ (grey) eccentric contractions (FIG. 2C). Treatment with colchicine (n=4) or apocynin (n=4) resulted in a significant protection from force loss (*p<0.05; ANOVA, NS, not significant vs. WT.
Figure 2A:
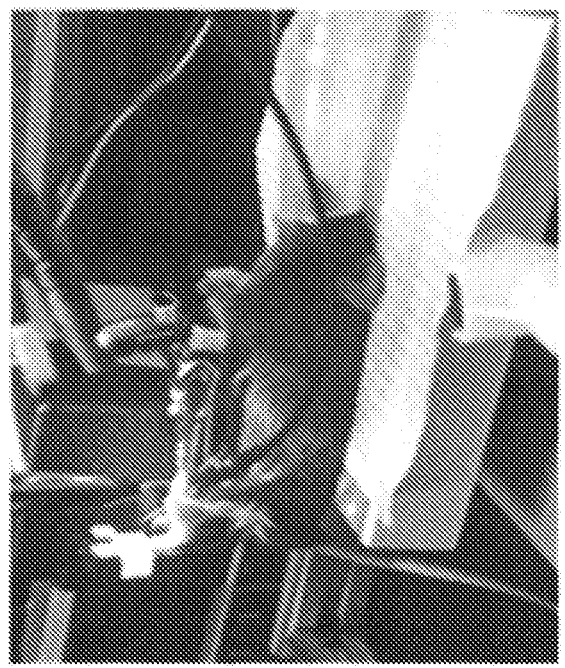
Figure 2D:
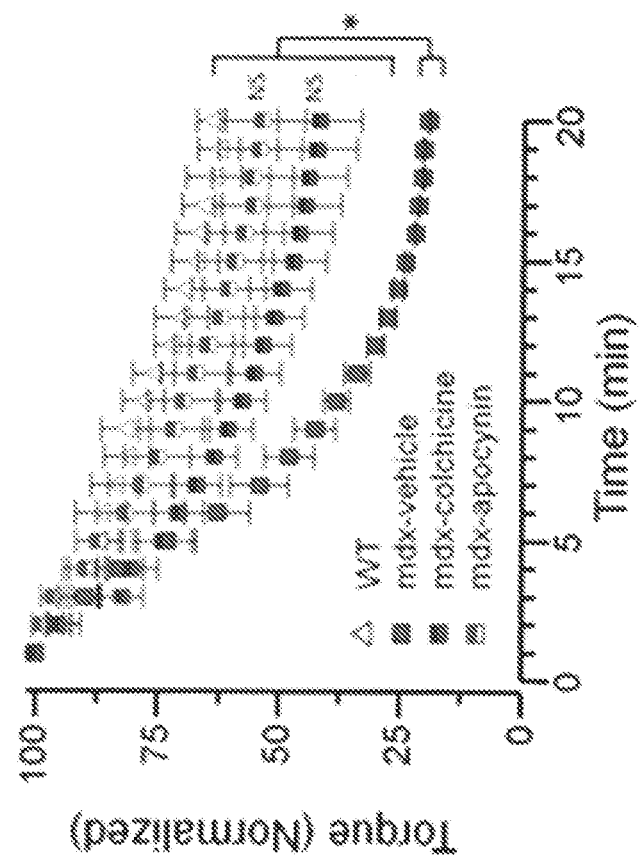
Figure 2C:
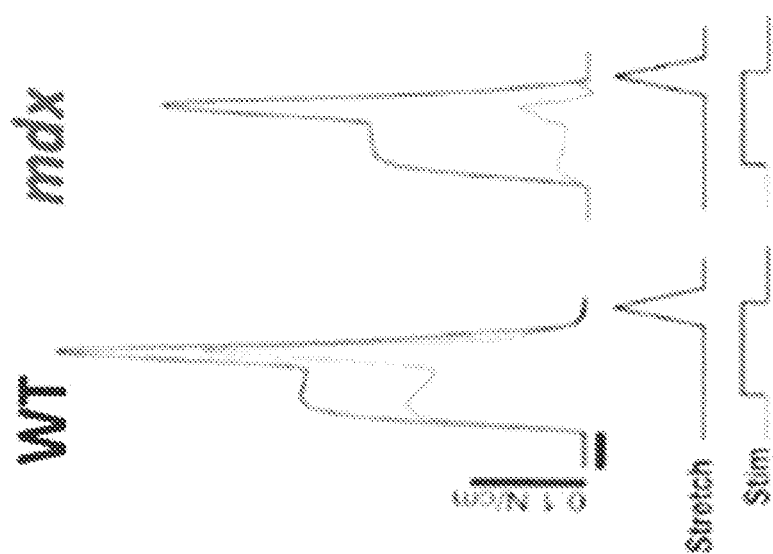

The disclosure provides novel pro-drugs, for example colchicinoid pro-drugs, that minimize the impact of the parent drug on the gastrointestinal epithelium resulting in improved absorption, and/or that exhibit improved PK profiles, e.g., increased half-life and delayed peak plasma concentrations. The disclosed colchicinoids pro-drugs enable safer and better tolerated clinical dosing regimens and more consistent therapeutic effects at tissue level.

Unless defined otherwise, all technical and scientific terms used herein have the same meaning as is commonly understood by one of skill in the art to which this invention belongs. All patents and publications referred to herein are incorporated by reference in their entireties.

Definitions

The term "active metabolite," as described herein, refers to a biologically active molecule that remains following metabolism (e.g., enzymatic or non-enzymatic hydrolysis) of a prodrug described herein, such as, for example, a prodrug of formula (I), formula (II), formula (III), formula (IV), formula (V), formula (VI), formula (VII), formula (VIII), formula (IX), or formula (X), or a pharmaceutically acceptable salt thereof. In some embodiments, the active metabolites described herein may be inhibitors of microtubule polymerization, such as colchicine, de-acetyl colchicine, colcemid, or nocodazole, or an analog thereof.

The terms "co-administration," "co-administering," "administered in combination with," "administering in combination with," "simultaneous," and "concurrent," as used herein, encompass administration of two or more pharmaceutical ingredients (e.g., two or more prodrugs and/or additional active agents) to a subject so that both pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, zinc, copper, and aluminum hydroxide and/or carbamate derivatives. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs disclosed herein, can also be incorporated into the described compositions and methods.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition).

"Prodrug" is intended to describe a compound that may be converted under physiological conditions or by enzymatic or non-enzymatic hydrolysis, for example, to provide a biologically active compound described herein. Thus, the term "prodrug" refers to a precursor of a biologically active compound that is pharmaceutically acceptable. A prodrug may be inactive when administered to a subject, but is converted in vivo to an active compound, for example, by enzymatic or non-enzymatic hydrolysis. The prodrug compound often offers the advantages of solubility, tissue compatibility or delayed release in a mammalian organism (see, e.g., Bundgaard, H., Design of Prodrugs (1985) (Elsevier, Amsterdam). The term "prodrug" is also intended to include any covalently bonded carriers, which release the active compound in vivo when administered to a subject.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$ where each $R^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $(C_{2-10})$alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., $(C_{2-10})$alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. $(C_{3-10})$cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbomyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl) heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)O$R^a$, —N($R^a$)C(O)$R^a$, —N($R^a$)C(O)N$(R^a)_2$, N($R^a$)C(N$R^a$)N$(R^a)_2$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a ($C_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)O$R^a$, —N($R^a$)C(O)$R^a$, —N($R^a$)C(O)N$(R^a)_2$, N($R^a$)C(N$R^a$)N$(R^a)_2$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)O$R^a$, —N($R^a$)C(O)$R^a$, —N($R^a$)C(O)N$(R^a)_2$, N($R^a$)C(N$R^a$)N$(R^a)_2$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C═O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)O$R^a$, —N($R^a$)C(O)$R^a$, —N($R^a$)C(O)N$(R^a)_2$, N($R^a$)C(N$R^a$)N$(R^a)_2$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —$N(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ substituents other than hydrogen, they can be combined with the nitrogen atom to form a 4-, 5-, 6- or 7-membered ring. For example, —$N(R^a)_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)O$R^a$, —N($R^a$)C(O)$R^a$, —N($R^a$)C(O)N$(R^a)_2$, N($R^a$)C(N$R^a$)N$(R^a)_2$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^a$, and NR$^a$R$^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., C$_1$-C$_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$O$R^a$ (where t is 1 or 2), —S(O)$_t$N$(R^a)_2$ (where t is 1 or 2), or PO$_3$$(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$O$R^a$ (where t is 1 or 2), —S(O)$_t$N$(R^a)_2$ (where t is 1 or 2), or PO$_3$$(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —$NO_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S($O_2$)—H, —S($O_2$)-(optionally substituted alkyl), —S($O_2$)-(optionally substituted amino), —S($O_2$)-(optionally substituted aryl), —S($O_2$)-(optionally substituted heteroaryl), and —S($O_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All embodiments of the invention can, in the alternative, be more specifically defined by any of the transitional terms "comprising," "consisting essentially of," and "consisting of."

Diseases Treatable by the Prodrugs Described Herein

In an embodiment, the prodrug compounds described herein may be used in the treatment of a disease ameliorated by inhibitors of microtubule polymerization. In some embodiments, such diseases may include, without limitation, Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF).

Duchenne's Muscular Dystrophy (DMD)

In an embodiment, a particular disease ameliorated by inhibitors of microtubule polymerization is DMD.

DMD is a devastating, life-limiting, X-linked neuromuscular disease affecting 1 out of every 2500 male births in the US. While afflicted DMD patients are born with relatively normal muscle function, the absence of dystrophin leads to a progressive and relentless deterioration of the skeletal muscle beginning late in the first year of life. While the average life expectancy for afflicted boys is around 24 years of age, the loss of muscle mass and function leaves most, if not all, wheelchair bound and on ventilator support for a significant portion of their lives.

DMD is an FDA-recognized orphan disease. To date there is only a single FDA-approved treatment for DMD. In September 2016, eteplirsen received accelerated FDA approval as a drug. Eteplirsen is a drug that promotes exon-skipping and works in only ~13% of DMD cases. Therefore, even with this recent approval, there is still a large unmet market need for the majority of DMD patients. Furthermore, of the four additional DMD drugs in clinical trials, two (both based on exon-skipping strategies) have been denied FDA approval due to lack of efficacy. Importantly, recent evidence suggests that blunting aberrant microtubule-dependent signaling can improve exon-skipping efficiency in DMD. This suggests that treatment with the prodrugs described herein could also provide an exceptional adjuvant to current clinical approaches and improve their efficacy.

Although the genetic basis for this deadly disease is known (i.e., lack of dystrophin), there are currently no genetic cures. Curative gene replacement necessitates systemic delivery of the dystrophin gene, and while viral delivery holds promise, there have been many obstacles including immunologic intolerance, inconsistent evidence of dystrophin production in biopsy, and failure to demonstrate a significant improvement in functional outcome measures. While targeted gene manipulation strategies are also being explored (i.e., CRISPR), there are over 2000 identified mutations in the dystrophin gene which suggests that effective strategies may only benefit a small number of patients. As patients await effective genetic therapies, there is a mandate by researchers, family support, organizations and the government to identify critical "downstream" events in the dystrophic process which can be therapeutically targeted to halt or slow the disease progression.

Dystrophin links the cytoskeleton of a muscle fiber or cardiac cell to its surrounding extracellular matrix through the dystrophin-glycoprotein complex. The absence of dystrophin results in a cascade of cellular alterations that impact many downstream pathways. The inventors have focused on reactive oxygen species (ROS) from NADPH Oxidase 2 (Nox2) and calcium ($Ca^{2+}$) signaling, which are pathways dysregulated early in DMD and whose exacerbation by muscle activity underscores the muscle injury and activation of pathological signaling cascades that drive disease progression.

In murine DMD (mdx), it has been discovered that disease-driven alterations in microtubule network density and properties underscore the deleterious excess of Nox2-ROS and $Ca^{2+}$ signals in skeletal muscle and heart. Using colchicine, a drug that promotes microtubule depolymerization, it has been shown that reducing microtubule density normalized the dysregulated ROS and $Ca^{2+}$ signaling in DMD muscle fibers in vitro (see FIG. 1). It has been further demonstrated that acute in vivo colchicine treatment reduced contraction injury in DMD mice (FIG. 2). Together, these results implicated the disease-altered microtubule network as a novel therapeutic target to effectively suppress the dysregulated ROS and $Ca^{2+}$ signaling in DMD muscle. The significance of these pre-clinical discoveries was bolstered by transcriptional evidence (RNASeq) for microtubule excess in muscle biopsy samples from affected DMD patients.

Without being limited to any one theory of the invention, it is determined that chronic administration of microtubule-targeted therapeutics have a broad impact on pathways impaired by dysregulated ROS and $Ca^{2+}$ signaling resulting in a slowing of disease progression in DMD. Furthermore, since exon-skipping efficiency is improved when dysregulated $Ca^{2+}$ signaling is blunted, it is proposed that microtubule-targeted strategies, such as the delivery of the prodrugs described herein may be complementary or necessary adjuncts for effective genetic approaches.

Prodrug Analogs of Microtubule Polymerization Inhibitors

In an embodiment, the prodrug compounds described herein include one or more compounds of formula (I), formula (II), formula (III), formula (IV), formula (V), formula (VI), formula (VII), formula (VIII), formula (IX), or formula (X), or a pharmaceutically acceptable salt thereof.

In an embodiment, the prodrug compounds described herein include prodrug analogs of colchicine, de-acetyl colchicine, colcemid, or nocodazole. In certain embodiments, the prodrug compound described herein is a prodrug analog of colchicine, de-acetyl colchicine, or colcemid.

Colchicine is a plant-derived bioactive molecule isolated from the autumn *crocus*. First used as a therapeutic in ancient Egypt, colchicine remains the most common microtubule depolymerizing agent used in clinical practice today. As the microtubule network is a critical component in the inflammatory response, colchicine and its congeners have proven effective in treating the symptoms of inflammation and pain in diverse pathological conditions, including gout, Familial Mediterranean Fever (FMF), pericarditis, Behcet's disease, and most recently, atrial fibrillation. It was only recently that colchicine underwent clinical trials for inflammatory gout, which garnered it FDA approval and patent protection, which has since expired. (i.e., Colcrys™). A discussion of colchicine and treatments of muscular conditions and muscular dystrophies is provided in U.S. Pat. No. 9,511,117, the entirety of which is incorporated by reference herein.

While acute colchicine treatment effectively suppresses dysregulated signaling, and improves function in the mdx mouse, its translation to the clinic may require establishing a dosing strategy that effectively manages the microtubule network long-term. To this end, colchicine's pharmacokinetic (PK) profile is not ideal for chronic use. The plasma concentration of orally dosed colchicine peaks in 30-90 min, with a half-life of 1-2.7 hours. Additionally, colchicine's effect on the microtubule structure in intestinal epithelial cells is responsible for a wide variability in absorption (24% to 88%; median 45%), which presents challenges in establishing an optimal dosing paradigm in patients. Furthermore, GI distress is often dose-limiting as seen in in FMF. Taken together with colchicine's relatively narrow therapeutic window (lethal dose: ~16-30× therapeutic dose), the short half-life and variable bioavailability present challenges when attempting to achieve a sustained target concentration within the tissue. Consequently, colchicine is used only acutely in response to gout flare-up, or limited dosing, which effectively manages the pathology in most patients with FMF.

Accordingly, the disclosure herein includes the development and validation of prodrugs, including colchicinoid prodrugs that may: (1) minimize impact on GI epithelium resulting in improved absorption; and/or (2) exhibit increased half-life and delayed peak plasma concentration. Together these improvements may enable safer and better tolerated clinical dosing regimens and more consistent therapeutic effects at the tissue level. The prodrugs described herein may fill a critical unmet medical need as a treatment to slow disease progression in DMD.

Figure 3:
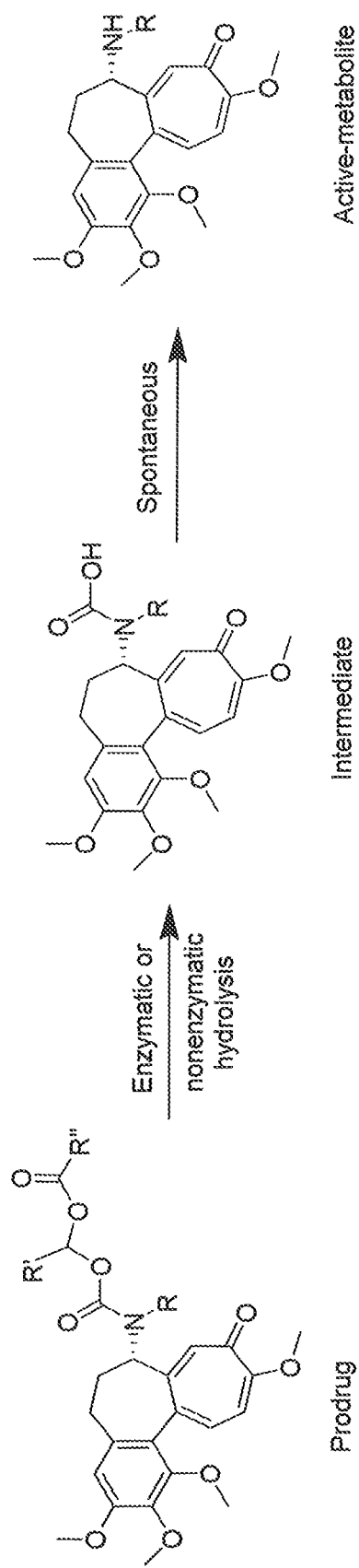
FIG. 3 illustrates an exemplary hydrolysis of an exemplary prodrug of the invention into the active-metabolite. The initial enzymatic hydrolysis is rate-limiting, whereas the second reaction resulting into the active-metabolite is expected to occur almost instantaneously.

Regarding colchicinoid prodrug analogs (e.g., prodrugs described herein based on colchicine and/or colcemid), in some embodiments, colchicine and analogs require the nitrogen group to be available for its action on microtubules. In some embodiments, chemically masking the essential nitrogen prevents an active metabolite from depolymerizing the microtubule cytoskeleton. In some embodiments, a reversible chemical masking group, such as a labile ester, masks the essential nitrogen until enzymatically removed (see FIG. 3). In some embodiments, small masking groups result in short extension of PK while longer bulkier groups extend PK more substantially. In some embodiments, modifying the masking group with polyethylene glycol (PEG) results in an extension in PK.

In an embodiment, the invention includes a prodrug of formula (I), formula (II) formula (III), formula (IV), or formula (V) (i.e., the "colchicinoid prodrug formulas"):

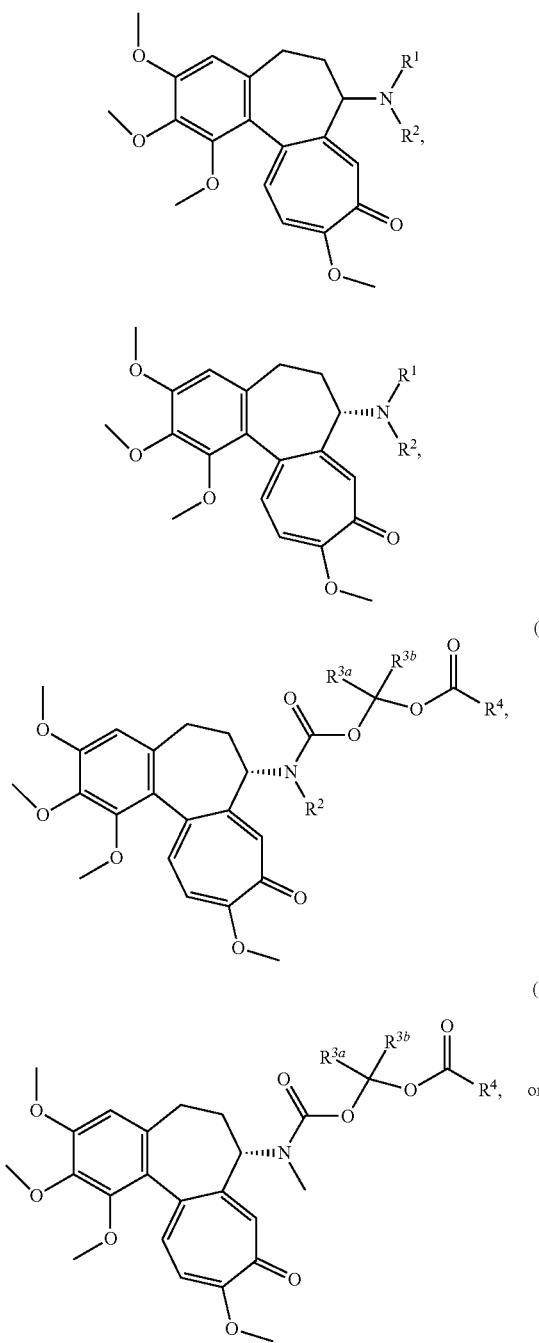

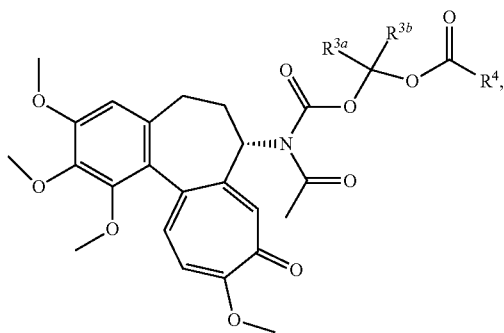

wherein $R^1$ may be a substituent selected from the group consisting of carboxyl, ester, and —C(=O)O-alkyl-OC(=O)-alkyl;

$R^2$ may be a substituent selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

$R^{3a}$ and $R^{3b}$ may be substituents independently selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

$R^4$ may be a substituent selected from the group consisting of H, and optionally substituted alkyl, alkoxy, -(alkoxy)$_n$-alkyl, heteroalkyl, and -(alkyl)$_n$-alkyl; n is an integer of 1-250; and the pharmaceutically acceptable salts thereof.

In some embodiments of the colchicinoid prodrug formulas, $R^1$ may be optionally substituted —C(=O)O-alkyl-OC(=O)-alkyl.

In some embodiments of the colchicinoid prodrug formulas, $R^2$ may be a substituent selected from the group consisting of H, and optionally substituted alkyl, aryl, ester, heteroaryl, and acyl.

In some embodiments of the colchicinoid prodrug formulas, $R^{3a}$ and $R^{3b}$ may be substituents independently selected from the group consisting of H, and optionally substituted alkyl, aryl, and heteroaryl.

In some embodiments of the colchicinoid prodrug formulas, $R^4$ may be a substituent selected from the group consisting of H, —CH$_3$, and optionally substituted —(CH$_2$)$_n$-alkyl, —(CH$_2$CH$_2$O)$_n$-alkyl, -(alkyl)$_n$-CH$_3$, and -(alkoxy)$_n$-CH$_3$, wherein n is an integer of 1-250.

In some embodiments of the colchicinoid prodrug formulas, n may be an integer of 1 to 10, or 10 to 20, or 20 to 30, or 30 to 40, or 40 to 50, or 50 to 60, or 60 to 70, or 70 to 80, or 80 to 90, or 90 to 100, or 100 to 110, or 110 to 120, or 120 to 130, or 130 to 140, or 140 to 150, or 150 to 160, or 160 to 170, or 170 to 180, or 180 to 190, or 190 to 200, or 200 to 210, or 210 to 220, or 220 to 230, or 230 to 240, or 240 to 250. In some embodiments, n may be an integer of 1 to 20, or 10 to 20.

In some embodiments of the colchicinoid prodrug formulas, wherein $R^4$ is —$(CH_2)_n$-alkyl, the alkyl may be methyl, and n may be an integer of 1 to 10, or 10 to 20, or 20 to 30, or 30 to 40, or 40 to 50, or 50 to 60, or 60 to 70, or 70 to 80, or 80 to 90, or 90 to 100, or 100 to 110, or 110 to 120, or 120 to 130, or 130 to 140, or 140 to 150, or 150 to 160, or 160 to 170, or 170 to 180, or 180 to 190, or 190 to 200, or 200 to 210, or 210 to 220, or 220 to 230, or 230 to 240, or 240 to 250. In some embodiments, n may be an integer of 1 to 20, or 10 to 20.

In some embodiments of the colchicinoid prodrug formulas, wherein $R^4$ is —$(CH_2CH_2O)_n$-alkyl, the alkyl may be methyl, and n may be an integer of 1 to 10, or 10 to 20, or 20 to 30, or 30 to 40, or 40 to 50, or 50 to 60, or 60 to 70, or 70 to 80, or 80 to 90, or 90 to 100, or 100 to 110, or 110 to 120, or 120 to 130, or 130 to 140, or 140 to 150, or 150 to 160, or 160 to 170, or 170 to 180, or 180 to 190, or 190 to 200, or 200 to 210, or 210 to 220, or 220 to 230, or 230 to 240, or 240 to 250. In some embodiments, n may be an integer of 1 to 20, or 1 to 10, or 10 to 20.

In some embodiments of the colchicinoid prodrug formulas, $R^2$ may be methyl or acetyl. In certain embodiments of the colchicinoid prodrug formulas, $R^2$ may be methyl.

In some embodiments of the colchicinoid prodrug formulas, $R^4$ may be a substituent selected from the group consisting of —$CH_3$, —$CH_2CH(CH_3)_2$, —$(CH_2)_{16}CH_3$, —$(CH_2CH_2O)_4$—$CH_3$, and —$(CH_2CH_2O)_{10}$—$CH_3$.

In some embodiments of the colchicinoid prodrug formulas, $R^{3a}$ and $R^{3b}$ may be H.

In some embodiments, the invention may include one or more of the colchicinoid prodrug analogs set forth below, which are encompassed by one or more of the colchicinoid prodrug formulas:

1

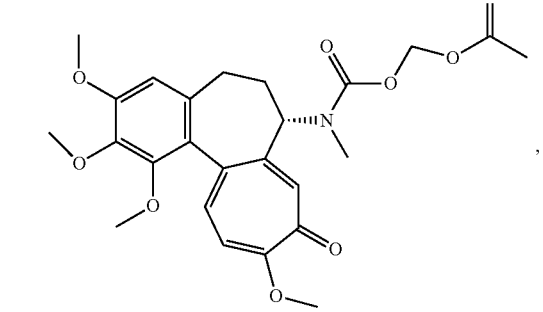

2

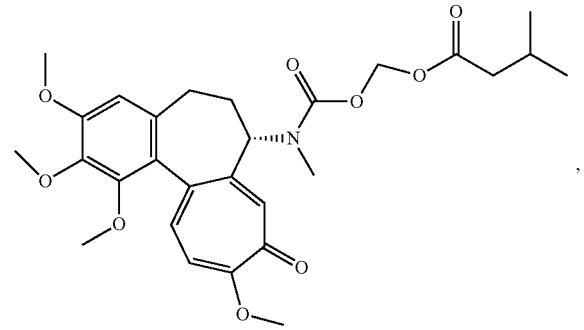

3

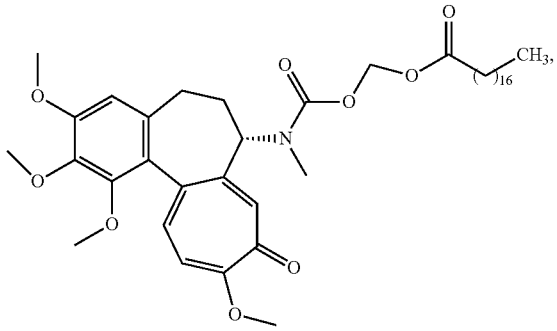

4

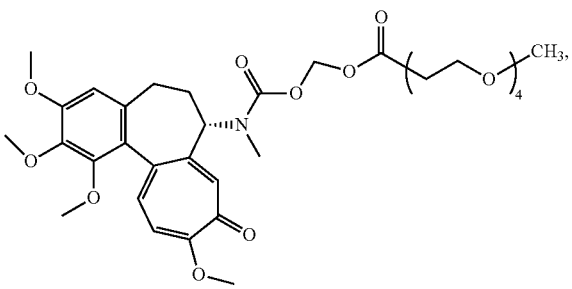

5

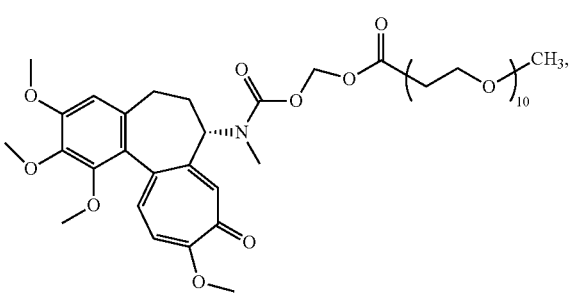

6

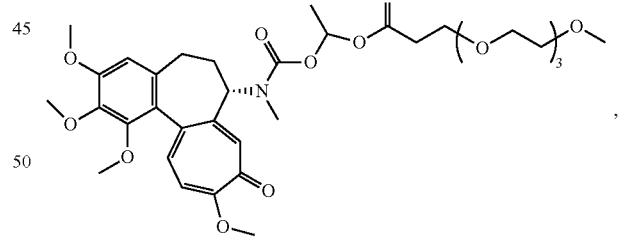

7

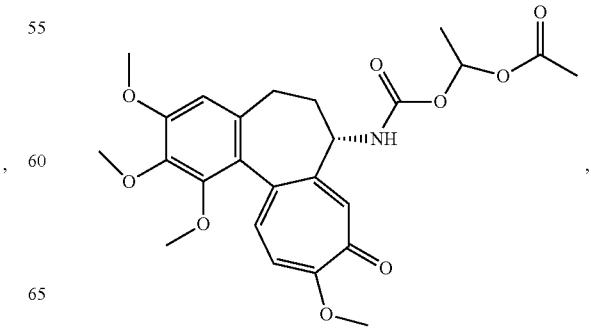

-continued

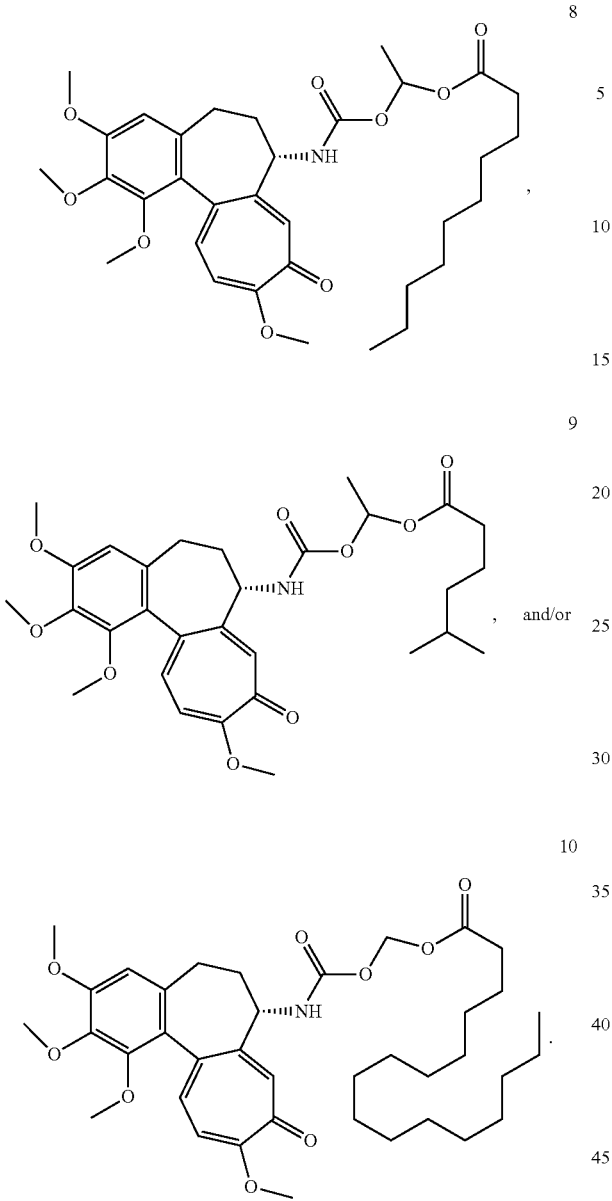

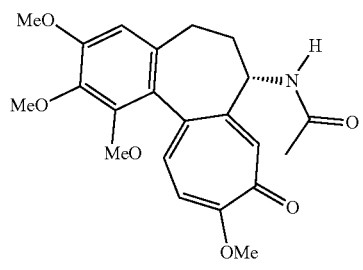
Colchicine

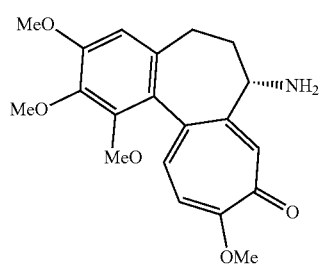
De-axetyl Colchicine

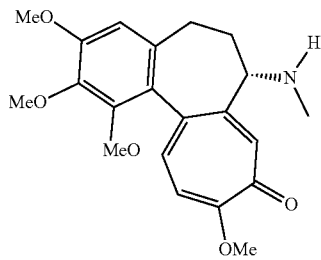
Colcemid

Nocodazole is an antineoplastic agent and inhibitor of microtubule polymerization. In some embodiments, the invention includes nocodazole prodrugs.

In an embodiment, the invention includes a prodrug of formula (VI), formula (VII), formula (VIII), formula (IX), or formula (X) (i.e., the "nocodazole prodrug formulas"):

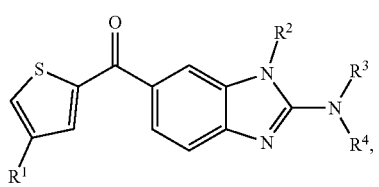
(VI)

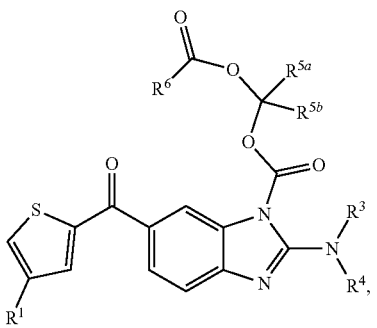
(VII)

In some embodiments of the colchicinoid prodrug formulas, the compounds thereof may exhibit a human or murine $C_{max}$ of 0.5 to 5 ng/ml, or 1 to 4 ng/ml, or less than 5 ng/ml, or less than 4 ng/ml, or less than 3 ng/ml, wherein the $C_{max}$ is not zero.

In some embodiments of the colchicinoid prodrug formulas, the compounds thereof may exhibit a human or murine half-life of 6 to 24 hours, or 8 to 18 hours, or 12 hours.

In some embodiments of the colchicinoid prodrug formulas, the compounds thereof may exhibit in at least a 50% decrease in force loss following 20 eccentric contractions in a human or murine model and/or at least a 50% increase in survival following isoproterenol cardiac stress in a human or murine model.

In some embodiments of the colchicinoid prodrug formulas, the active metabolite of the compounds thereof may be colchicine, de-acetyl colchicine, or colcemid.

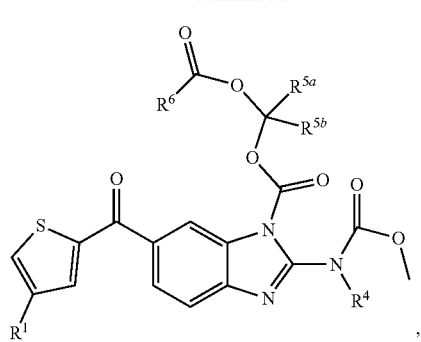

(VIII)

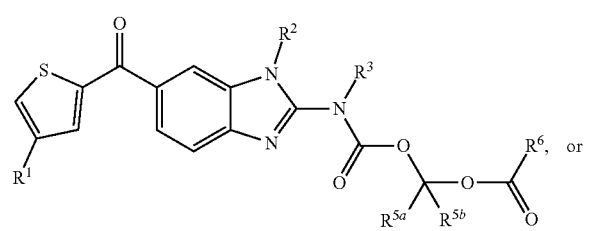

(IX)

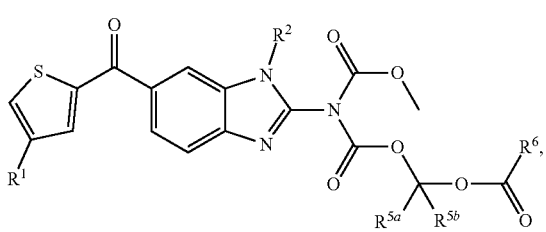

(X)

wherein R¹ may be a substituent selected from the group consisting of H, and optionally substituted alkyl, -alkyl-CN, alkyl-ester, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

R² may be a substituent selected from the group consisting of H, and optionally substituted alkyl, carboxyl, ester, and —C(=O)O-alkyl-OC(=O)-alkyl;

R³ may be a substituent selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

R⁴ may be a substituent selected from the group consisting of H, and optionally substituted alkyl, carboxyl, ester, and —C(=O)O-alkyl-OC(=O)-alkyl;

R$^{5a}$ and R$^{5b}$ may be substituents independently selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

R⁶ may be a substituent selected from the group consisting of H, and optionally substituted alkyl, alkoxy, -(alkoxy)$_n$-alkyl, heteroalkyl, and -(alkyl)$_n$-alkyl; n is an integer of 1-250; and the pharmaceutically acceptable salts thereof.

In some embodiments of the nocodazole prodrug formulas, R¹ may be selected from the group consisting of H, and optionally substituted alkyl, —(CH$_2$)$_m$—CN, —(CH$_2$)$_m$—C(=O)OH, and —(CH$_2$)$_m$—C(=O)O-alkyl, wherein m is an integer of 1 to 10.

In some embodiments of the nocodazole prodrug formulas, R² may be H or optionally substituted —C(=O)O-alkyl-OC(=O)-alkyl.

In some embodiments of the nocodazole prodrug formulas, R³ may be a substituent selected from the group consisting of H, and optionally substituted alkyl, aryl, ester, heteroaryl, and acyl.

In some embodiments of the nocodazole prodrug formulas, R⁴ may be H or optionally substituted —C(=O)O-alkyl-OC(=O)-alkyl.

In some embodiments of the nocodazole prodrug formulas, R² may be optionally substituted —C(=O)O-alkyl-OC(=O)-alkyl and R⁴ is H.

In some embodiments of the nocodazole prodrug formulas, R² is H and R⁴ may be optionally substituted —C(=O)O-alkyl-OC(=O)-alkyl.

In some embodiments of the nocodazole prodrug formulas, R$^{5a}$ and R$^{5b}$ may be independently selected from the group consisting of H, and optionally substituted alkyl, aryl, and heteroaryl.

In some embodiments of the nocodazole prodrug formulas, R⁶ may be a substituent selected from the group consisting of H, —CH$_3$, and optionally substituted —(CH$_2$)$_n$-alkyl, —(CH$_2$CH$_2$O)$_n$-alkyl, -(alkyl)$_n$-CH$_3$, and -(alkoxy)$_n$-CH$_3$, wherein n is an integer of 1-250.

In some embodiments of the nocodazole prodrug formulas, n may be an integer of 1 to 10, or 10 to 20, or 20 to 30, or 30 to 40, or 40 to 50, or 50 to 60, or 60 to 70, or 70 to 80, or 80 to 90, or 90 to 100, or 100 to 110, or 110 to 120, or 120 to 130, or 130 to 140, or 140 to 150, or 150 to 160, or 160 to 170, or 170 to 180, or 180 to 190, or 190 to 200, or 200 to 210, or 210 to 220, or 220 to 230, or 230 to 240, or 240 to 250.

In some embodiments of the nocodazole prodrug formulas, wherein R⁶ may be —(CH$_2$)$_n$-alkyl, the alkyl may be methyl, and n may be an integer of 1 to 10, or 10 to 20, or 20 to 30, or 30 to 40, or 40 to 50, or 50 to 60, or 60 to 70, or 70 to 80, or 80 to 90, or 90 to 100, or 100 to 110, or 110 to 120, or 120 to 130, or 130 to 140, or 140 to 150, or 150 to 160, or 160 to 170, or 170 to 180, or 180 to 190, or 190 to 200, or 200 to 210, or 210 to 220, or 220 to 230, or 230 to 240, or 240 to 250. In some embodiments, n may be an integer of 1 to 20, or 10 to 20.

In some embodiments of the nocodazole prodrug formulas, wherein R⁶ may be —(CH$_2$CH$_2$O)$_n$-alkyl, the alkyl may be methyl, and n may be an integer of 1 to 10, or 10 to 20, or 20 to 30, or 30 to 40, or 40 to 50, or 50 to 60, or 60 to 70, or 70 to 80, or 80 to 90, or 90 to 100, or 100 to 110, or 110 to 120, or 120 to 130, or 130 to 140, or 140 to 150, or 150 to 160, or 160 to 170, or 170 to 180, or 180 to 190, or 190 to 200, or 200 to 210, or 210 to 220, or 220 to 230, or 230 to 240, or 240 to 250. In some embodiments, n may be an integer of 1 to 20, or 1 to 10, or 10 to 20.

In some embodiments of the nocodazole prodrug formulas, $R^1$ may be H.

In some embodiments of the nocodazole prodrug formulas, $R^3$ may be methyl or an alkyl ester (e.g., methyl ester).

In some embodiments of the nocodazole prodrug formulas, $R^6$ may be a substituent selected from the group consisting of —CH$_3$, —CH$_2$CH(CH$_3$)$_2$, —(CH$_2$)$_{16}$CH$_3$, —(CH$_2$CH$_2$O)$_4$—CH$_3$, and —(CH$_2$CH$_2$O)$_{10}$—CH$_3$.

In some embodiments of the nocodazole prodrug formulas, $R^{5a}$ and $R^{5b}$ may be H.

In some embodiments of the nocodazole prodrug formulas, the compounds thereof may exhibit a human or murine $C_{max}$ of 0.5 to 5 ng/ml, or 1 to 4 ng/ml, or less than 5 ng/ml, or less than 4 ng/ml, or less than 3 ng/ml, wherein the $C_{max}$ is not zero.

In some embodiments of the nocodazole prodrug formulas, the compounds thereof may exhibit a human or murine half-life of 6 to 24 hours, or 8 to 18 hours, or 12 hours.

In some embodiments of the nocodazole prodrug formulas, the compounds thereof may exhibit in at least a 50% decrease in force loss following 20 eccentric contractions in a human or murine model and/or at least a 50% increase in survival following isoproterenol cardiac stress in a human or murine model.

In some embodiments of the nocodazole prodrug formulas, the active metabolite of the compounds thereof may be nocodazole:

Nocodazole

Pharmaceutical Compositions

In an embodiment, the invention provides a pharmaceutical composition for use in the treatment of the diseases and conditions described herein. In a preferred embodiment, the invention provides pharmaceutical compositions, including those described below, for use in the treatment of Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF). In a preferred embodiment, the invention provides pharmaceutical compositions, including those described below, for use in the treatment of DMD.

The pharmaceutical compositions are typically formulated to provide a therapeutically effective amount of a prodrug described herein, or a pharmaceutically acceptable salt, solvate, or hydrate thereof, as the active ingredient. Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

The pharmaceutical compositions described above are preferably for use in the treatment of the Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF). In a preferred embodiment, the pharmaceutical compositions are for use in the treatment of DMD.

In some embodiments, the concentration of a prodrug provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of a prodrug provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of a prodrug provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of a prodrug provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of a prodrug provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of a prodrug provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Each of the prodrugs provided according to the invention is effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Pharmaceutical Compositions for Oral Administration

In preferred embodiments, the invention provides a pharmaceutical composition for oral administration containing a prodrug described herein, and a pharmaceutical excipient suitable for administration.

In preferred embodiments, the invention provides a solid pharmaceutical composition for oral administration containing: (i) an effective amount of a compound of the colchicinoid prodrug formulas and (ii) a pharmaceutical excipient suitable for administration. In some embodiments, the composition further contains (iii) an effective amount of an additional active pharmaceutical ingredient.

In some embodiments, the invention provides a solid pharmaceutical composition for oral administration containing: (i) an effective amount of a compound of the nocodazole prodrug formulas and (ii) a pharmaceutical excipient suitable for administration. In some embodiments, the composition further contains (iii) an effective amount of an additional active pharmaceutical ingredient.

In some embodiments, the additional active pharmaceutical ingredient may include one or more of a non-glucocorticoid steroid (e.g., a bile acid, a bis-nor- or etiocholanic acid, a spriostane, a sterol, an androstane, an estrane, a pregnane, an estratriene, and/or a cardenolide, see, e.g., U.S. Patent Application Publication No. 2007/0259837), a compound that increases utrophin expression (see, e.g., U.S. Patent Application Publication No. 2011/0135638), biglycan (see, e.g., U.S. Pat. Nos. 7,612,038, 8,138,154, and 8,691,766), eteplirsen (see, U.S. Pat. No. 9,506,058), 5-(ethylsulfonyl)-2-(naphthalen-2-yl)benzo[d]oxazole (see, U.S. Published Patent Application No. 2009/0048314 and U.S. Pat. No. 9,492,433), prednisone (e.g., 0.75 mg/kg, daily), and deflazacort (e.g., 0.9 mg/kg, daily). In some embodiments, additional active pharmaceutical ingredients include one or more of those compounds and/or compositions disclosed by U.S. Patent Application Publication Nos. 2005/0158281, 2007/0259837, 2009/0048314, 2010/0168072, and 2011/0135638, and U.S. Pat. Nos. 7,612,038, 8,138,154, 8,691,766, 9,492,433, and 9,506,058, the entirety of which are incorporated herein by reference.

In some embodiments, the pharmaceutical composition may be a liquid pharmaceutical composition suitable for oral consumption.

Pharmaceutical compositions of the invention suitable for oral administration can be presented as discrete dosage forms, such as capsules, sachets, tablets, liquids, or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the prodrug ingredient(s) into association with the carrier, which constitutes one or more necessary ingredients. In general, the compositions are prepared by uniformly and intimately admixing the prodrug ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

The prodrug ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; camitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; camitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, 6-valerolactone and isomers thereof, (3-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In preferred embodiments, the invention provides a pharmaceutical composition for injection containing a prodrug described herein, and a pharmaceutical excipient suitable for injection. Components and amounts of prodrugs in the compositions are as described herein.

The forms in which the compositions of the invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating a prodrug described herein in the required amounts in the appropriate solvent with various other ingredients as enumerated above, as required, followed by filtered sterilization. Generally, dispersions are prepared by incorporating the various sterilized prodrug ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In preferred embodiments, the invention provides a pharmaceutical composition for transdermal delivery containing a prodrug described herein, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the prodrug ingredients. In contrast, a solution formulation may provide more immediate exposure of the prodrug ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a prodrug described herein in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001, 139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of a prodrug described herein or a pharmaceutical composition of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The prodrugs described herein can also be administered intraadiposally or intrathecally.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. A prodrug described herein may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. A prodrug described herein may additionally be administered intravascularly from a balloon used during angioplasty. Extravascular administration of a prodrug described herein via the pericard or via advential application of formulations of the invention may also be performed to decrease restenosis.

Exemplary parenteral administration forms include solutions or suspensions of a prodrug compound in sterile aqueous solutions, for example, aqueous propylene glycol or dextrose solutions. Such dosage forms can be suitably buffered, if desired.

The invention also provides kits. The kits include a prodrug described herein in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In some embodiments, the prodrug described herein and another active pharmaceutical ingredient are provided as separate compositions in separate containers within the kit. In some embodiments, the prodrug and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The kits described above are preferably for use in the treatment of the diseases and conditions described herein. In a preferred embodiment, the kits are for use in the treatment of DMD.

In a preferred embodiment, the kits of the present invention are for use in the treatment of Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, or Familial Mediterranean Fever (FMF).

Dosages and Dosing Regimens

The amounts of a prodrug described herein administered will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of a prodrug described herein may be provided in units of mg/kg of body mass or in mg/m$^2$ of body surface area.

In some embodiments, a prodrug described herein is administered in multiple doses. In a preferred embodiment, a prodrug described herein is administered in multiple doses. Dosing may be once, twice, three times, four times, five times, six times, or more than six times per day. Dosing may be once a month, once every two weeks, once a week, or once every other day. In other embodiments, a prodrug described herein is administered about once per day to about 6 times per day. In some embodiments, a prodrug described herein is administered once daily, while in other embodiments, a prodrug described herein is administered twice daily, and in other embodiments a prodrug described herein is administered three times daily.

Administration a prodrug described herein may continue as long as necessary. In some embodiments, a prodrug described herein is administered for more than 1, 2, 3, 4, 5, 6, 7, 14, or 28 days. In some embodiments, a prodrug described herein is administered for less than 28, 14, 7, 6, 5, 4, 3, 2, or 1 day. In some embodiments, a prodrug described herein is administered chronically on an ongoing basis—e.g., for the treatment of chronic effects. In another embodiment, the administration of t a prodrug described herein continues for less than about 7 days. In yet another embodiment, the administration continues for more than about 6, 10, 14, 28 days, two months, six months, or one year. In some cases, continuous dosing is achieved and maintained as long as necessary.

In some embodiments, an effective dosage of a prodrug described herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or 198 mg to about 202 mg.

In some embodiments, an effective dosage of a prodrug described herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of a prodrug described herein may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Methods of Treating Diseases Alleviated by Microtubule-Targeted Therapeutics and Prodrugs Thereof The compositions and prodrugs described above can be used in a method for treating disorders and diseases alleviated by microtubule-targeted therapeutics, such as diseases alleviated by colchicine, colcemid, and/or nocodazole. In a preferred embodiment, they are for use in treating DMD. They may also be used in treating other disorders as described herein and in the following paragraphs.

In some embodiments, the disorders and diseases alleviated by microtubule-targeted therapeutics may include one of Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF).

In some embodiments, the invention provides a method of treating a disease described herein with a composition including a prodrug described herein, wherein the dose is effective to inhibit microtubule polymerization. In some embodiments, the invention provides a method of treating Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF), wherein the inhibit microtubule polymerization.

In an embodiment, the invention includes a method of treating a disease selected from the group consisting of Duchenne's Muscular Dystrophy (DMD), Becker's Muscular Dystrophy, Congenital Muscular Dystrophy, heart failure, desminopathy, cardiomyopathy, inclusion body myositis, autoimmune myositis, tau related myopathies, Limb Girdle Muscular Dystrophy, Sarcopenia, Osteoporosis, Atrial Fibrillation, pericarditis, Behcet's disease, inflammatory gout, and Familial Mediterranean Fever (FMF), in a patient in need of such treatment, the method including the step of administering a therapeutically effective amount of a prodrug of described by a colchicinoid prodrug formula or a nocodazole prodrug formula, or a pharmaceutically acceptable salt thereof, and a pharmaceutically acceptable carrier.

In some embodiments, the methods described herein may further include the step of administering an exon-skipping therapy, to a patient in need of such therapy, before, after, or concomitantly with a pharmaceutical composition described herein. Such exon-skipping therapies are disclosed, for example, in U.S. Pat. Nos. 8,865,883 and 9,506,058, the entirety of which is incorporated herein by reference.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Method of Determining Microtubule Depolymerization Activity

Following chemical synthesis, it can be confirmed that the prodrugs described herein are able to depolymerize microtubules in muscle cell cultures in vitro, as described in Nat. Commun. (2015) 6:8526. Briefly, C2C12 cells (ATCC, Manassas Va.) can be cultured according to standard protocols. Original cell aliquots representing approximately 20 million cells can be thawed and seeded into T75 flasks in DMEM supplemented with 10% FBS and 2% penicillin-streptomycin and grown in a humidified incubator with 5% $CO_2$ at 37° C. Media can be replaced every 2 to 3 days and cells allowed to grow to 80% confluency. Once 80% confluency is achieved, serum is removed and myoblasts allowed to fuse and form myotubes. Fused myotubes are then treated with vehicle, colchicine or one of the prodrugs recited herein at 0.01, 0.03, 0.1, 0.3, 1 and 3 mg/ml overnight. Following incubation, the cells are rinsed with warm saline, then fixed with 4% paraformaldehyde, permeabilized with 0.1% triton, then incubated with antibodies to α-tubulin and actin overnight, appropriate fluorescent secondary antibodies are applied, and slides imaged on a fluorescent confocal microscope and MT density quantified.

Following in vitro efficacy measurements, the PK of each compound can be assessed at 3 doses determined from the preliminary in vitro data. For example, given that some of the formulations are prodrugs of colchicine, the levels of colchicine in circulating plasma can be measured up to 48 h after administration. Briefly, following one week of acclimation, prodrug can be delivered intraperitoneally (IP) to 12-week old DBA/2 mice. At different time points (0.5, 1, 3, 6, 9, 12, 24 and 48 h) following administration, 5 mice can be euthanized and blood and tissues collected. Measurements of colchicine levels can be performed using an LC/MS/MS protocol. A similar strategy may be employed for prodrugs of nocodazole.

Figure 4:
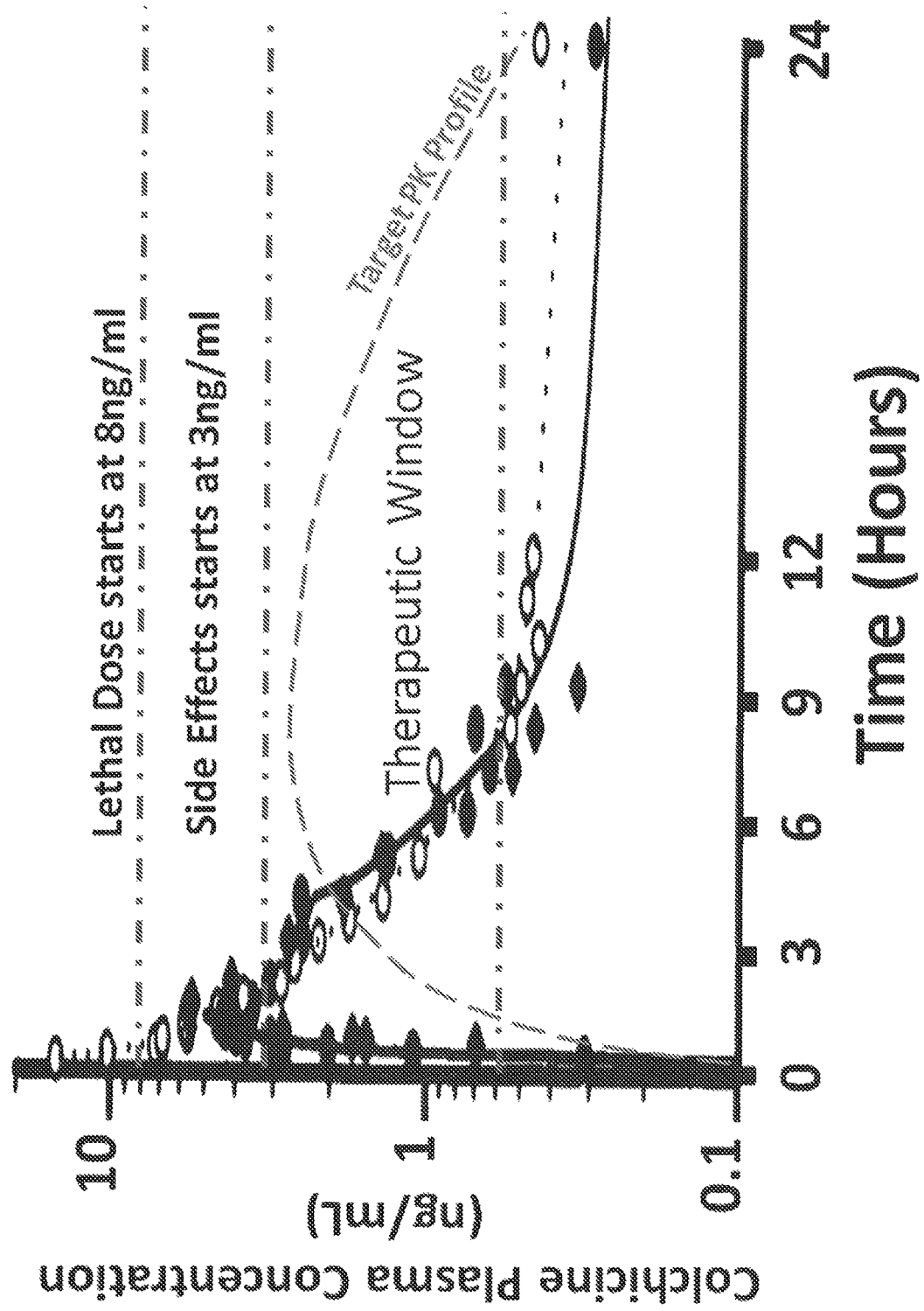
FIG. 4 illustrates the pharmacokinetics of colchicine in a human subject after a single dose of 1 mg. Colchicine was administered either orally (closed circles) or intravenously (open circles). The dashed blue line represents the target PK profile of a prodrug analog (e.g., a colchicine prodrug analog) described herein.
Figure 5A:
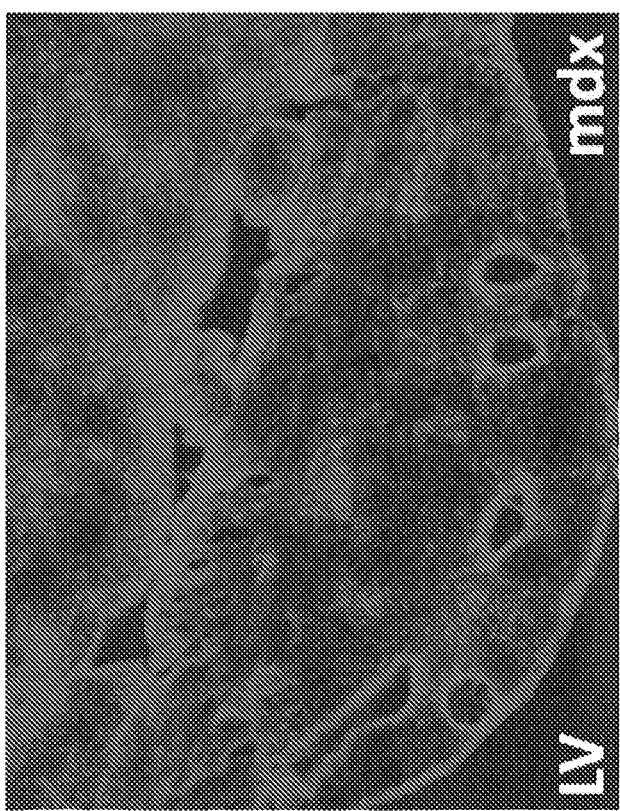
FIGS. 5A-5D illustrate that colchicine blunts isoproterenol-induced cardiac damage in mdx and prevents cardiac arrhythmias. Wild-type and mdx mice were injected with Evan's blue dye one day prior then underwent an isoproterenol cardiac stress test and heart rate measured. Upon isoproterenol infusion, WT mice had their heart rate increase ~3 fold for approximately 2 hours, prior to returning to baseline and displayed no cardiac damage. Conversely, mdx mice cannot upregulate their heart rate to the same extent (~2 fold) and only do so for a short period (30-45 min) before suffering severe arrhythmias and cardiac death, with only 10% survival. Histological analysis reveals large areas of necrosis as evidenced by Evan's blue positive cells (FIGS. 5A and 5B). Colchicine prevents cardiac death and arrhythmia (90% survival) and supports the increase in cardiac workload significantly compared to untreated animals. Histological analysis reveals significant preservations of cardiac integrity (FIGS. 5C and 5D).
Figure 5B:
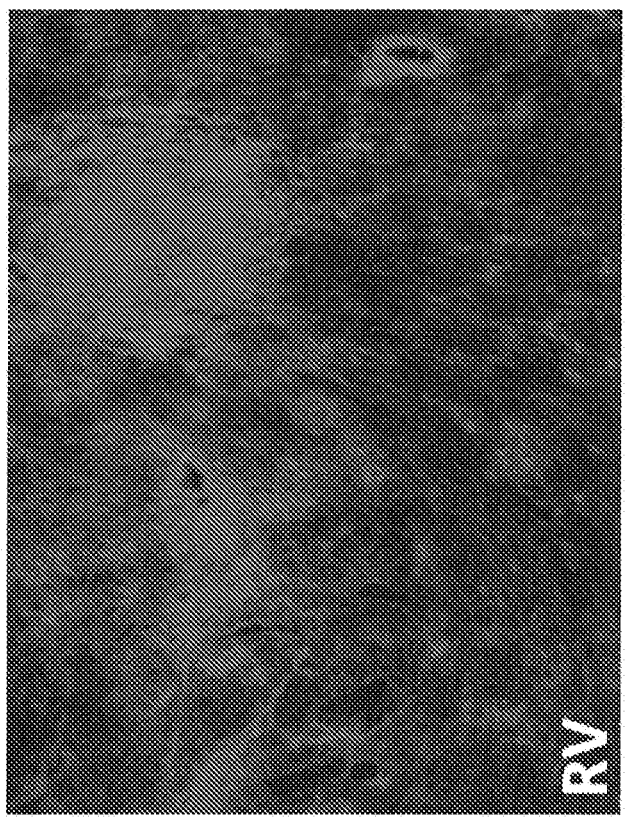
Figure 5C:
Figure 5D:
Figure 6A:
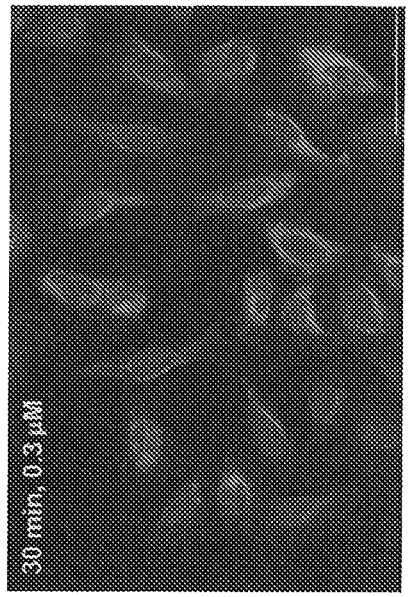
FIGS. 6A-6G illustrate depolymerization studies in OCY-293 cells stably expressing GFP-tubulin upon treatment with colchicine on a time course for 10 minutes, 20 minutes, 30 minutes, 45 minutes, 60 minutes, and 90 minutes, at 0.3 µM, 1 µM, 10 µM, and 100 µM (FIGS. 6A-6F: imaging results for 0.3 µM colchicine at 10 minutes, 20 minutes, 30 minutes, 45 minutes, 60 minutes, and 90 minute.
Figure 6C:
Figure 6B:
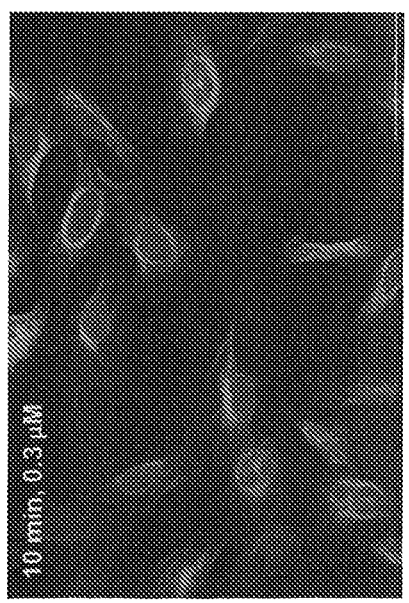
Figure 6D:
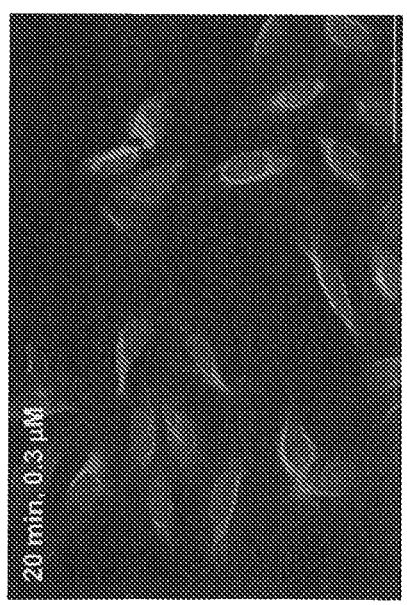
Figure 6G:
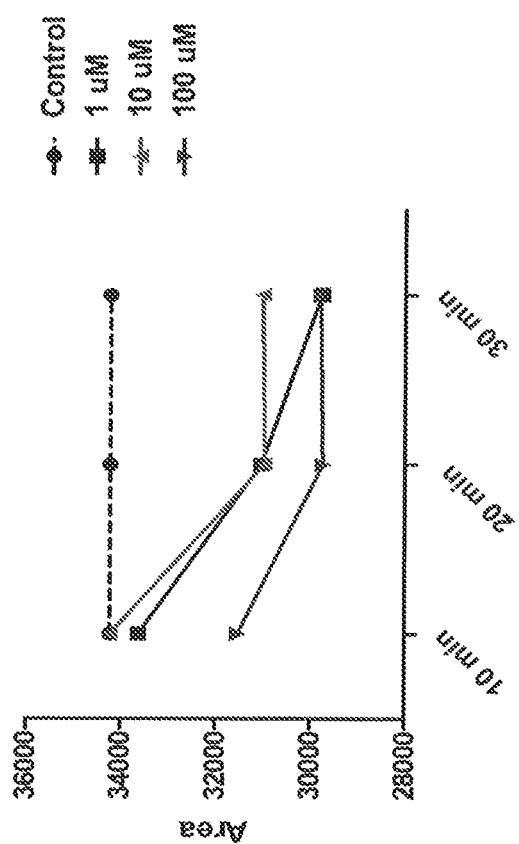
Figure 6E:
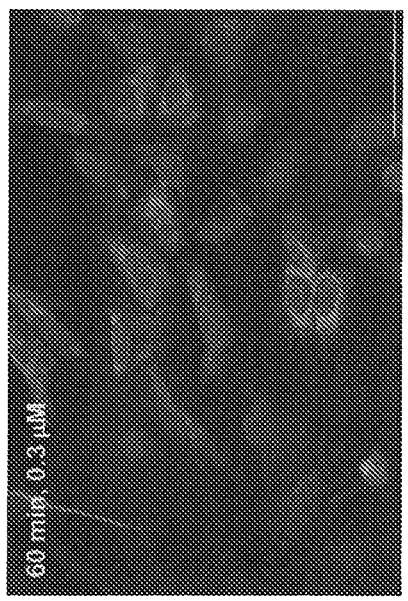
Figure 6F:
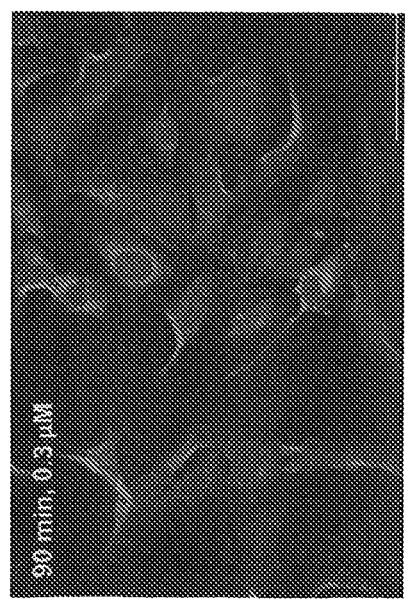

Success criteria for the prodrugs described herein may be, for example, screening for compounds that exhibit a $C_{max}$ of 3 ng/ml or less in blood, a half-life of at least 12 h and a general PK profile similar to that shown in FIG. 4.

Example 2—In Vivo Evaluation of Prodrug Compounds Described Herein

D2.mdx or their congenic control mice (DBA/2) can be dosed with the prodrugs described herein, daily I.P. for one week with either vehicle or one of three doses of a specific prodrug as determined from the PK results Example 1 (See Table 2 for details).

Table: In Vivo Efficacy Groupings

| Group | Strain | Dose | N | Assays |
|---|---|---|---|---|
| 1 | DBA/2 | Vehicle—Volume Matched | 16 | Acclimate mice for 7 days 7 days of daily IP dosing |
| 2 | D2.mdx | Vehicle—Volume Match | 16 | Divide all treatment groups into 2 separate functional |
| 3 | D2.mdx | Lowest Dose—1/3 of Group 4 | 16 | tests In Vivo Eccentric Injury, |
| 4 | D2.mdx | Optimal Dose from Aim 1 | 16 | n = 8 Cardiac Stress, n = 8 |
| 5 | D2.mdx | Highest Dose—3x Group 4 | 16 | Perform Histology, Biochemistry and Calpain Activity Assay on all animals |

One day before testing, animals can be administered Evan's blue dye (5 μg/μl solution in PBS; 5 μl/g body weight) to assay sarcolemmal integrity in the heart and muscles. At the end of the dosing period, each treatment group can be divided into 2 subgroups for (1) in vivo eccentric injury, and (2) isoproterenol challenge and cardiac stress. Following the testing, animals can be sacrificed and blood and tissues collected for further analysis. Muscle and heart can be prepared for histology and cell integrity determined as % of cells that are positive for Evan's blue dye. Additionally, molecular and biochemical assays can be to measure levels of microtubules, calpain activity and fibrosis.

End-Point In Vivo Measures.

Following the treatment period, pre-clinical end-point measures of muscle and heart integrity can be used to gauge treatment efficacy.

Skeletal Muscle Function.

Evan's blue dye (EBD) (5 μg/l solution in PBS; 5 μl/g body weight) can be injected I.P. 24 hrs before the assay. The in vivo assessment of the nerve evoked isometric force vs. stimulation frequency relationship of the gastrocnemius can be determined as described in the art. The maximal isometric force (post hoc normalized to estimated cross sectional area) can be taken as the measure of functional quality of the muscle. Here, an increase in total force or force normalized post hoc to muscle cross sectional area can be taken as evidence of treatment efficacy.

Susceptibility to contraction injury (skeletal muscle) can be assessed across each treatment cohort. As in FIG. 2, the % force deficit after 20 eccentric contractions of the gastrocnemius muscle can be determined. A reduction in the % force deficit with treatment can be taken as an indication of treatment efficacy. Thirty minutes after the last eccentric contraction, blood (orbital sinus) can be collected and analyzed for creatine kinase (CK) activity. The gastrocnemius from both un-stimulated (rest) and stimulated leg (eccentric contraction) are harvested as described below. After the trials, the muscle tissue can be processed and % EBD positive fibers can be used to quantitate the extent of muscle damage at rest (uninjured leg) or with injury.

Isoproterenol Cardiac Stress and Sarcolemmal Damage of the Heart.

Catecholaminergic work-load stress induces atrial fibrillation (AF), ventricular tachycardia (VT) and sudden cardiac death (SCD) in mdx mice and this can be prevented by colchicine treatment (FIG. 5). To assess if colchicine prodrugs prevent AF, VT and SCD, Evan's blue dye (EBD) (5 µg/µl solution in PBS; 5 µl/g body weight) can be injected I.P. 24 hrs before the assay. Mice are first anesthetized with sodium pentobarbital, and the heart rate monitored by a single-lead electrocardiogram. Isoproterenol is then used to pharmacologically increase the level of mechanical stress imposed on the heart. The mice are killed 3 hours after the administration of isoproterenol and the heart mounted in cryomatrix, sectioned and assessed for sarcolemmal damage.

Necropsy, Blood and Tissue Collection and Histology.

At the time of euthanasia, blood can be collected via cardiac puncture. Tissues collected can be the gastrocnemius, soleus, tibialis anterior, extensor digitorum longus, quadriceps, diaphragm, heart, liver, lung, kidney, spleen. The gastroc and the heart that underwent injury can be isolated, weighed and mounted in embedded in cryomatix and frozen in 2-methylbutane cooled in dry ice. All tissues can be kept at −80° C. Samples frozen for histology can be embedded in cryomatrix on a soft cork surface and serially sectioned (10 µm thickness) perpendicular to the fiber axis. Multiple slices (5-10) can be taken at different portions of the muscle. The slices are then either frozen unfixed or fixed in ice-cold paraformaldehyde and kept at −80° C. until further use. Histological endpoints can include necrosis, centrally nucleated myofibers, fibrosis, fiber number, fiber diameter, alizarin red calcium staining and NADPH staining.

Calpain Activity Assay.

In DMD muscle, the increase in calcium cycling leads to an increase in calpain proteolysis that modifies numbers proteins and signaling pathways. Measurement of in-situ calpain activity can be performed. The synthetic calpain substrate (7-amino-4-chloromethyl-coumarin-t-butoxycarbonyl-L-leucyl-L-methionine amide; Boc-Leu-Met-CMAC)) reports real-time activity of both µ- and m-calpain activity. In its native form Boc-Leu-Met-CMAC is permeable to the cell where it is modified to Boc-Leu-Met-MAC-SG by the glutathione S-transferase, transforming the substrate to an impermeable form. Upon calpain cleavage the fluorescent product (MAC-SG, 7-amino-4-methylcoumarin glutathione conjugate; ex: 380 nm, em; 480 nm) is liberated and tracked as a real-time reflection of calpain activity.

Immunoprecipitation/Immunoblot.

Tissues from WT and mdx age-matched littermates can be prepared for immunoprecipitation and/or immunoblot, separated by PAGE and probed for alpha-tubulin, glu-tubulin, GAPDH and using commercially available reagents as previously described. Immunoblots can be imaged and quantified with an Odyssey infrared imaging system (LICOR Biosystems) and appropriate infrared-labeled secondary antibodies.

Data Analysis and Statistics.

Comparisons between multiple groups can be performed by one-way analysis of variance (ANOVA) for parametric data or by Kruskal-Wallis one-way analysis of variance on ranks for nonparametric data using SigmaPlot 13 software (San Jose, Calif.). A P-value <0.05 can be considered statistically significant.

Example 3—Exemplary Synthesis of Colcemid Prodrug Compound 6

Colcemid prodrug compound 6 may be prepared according to the following scheme:

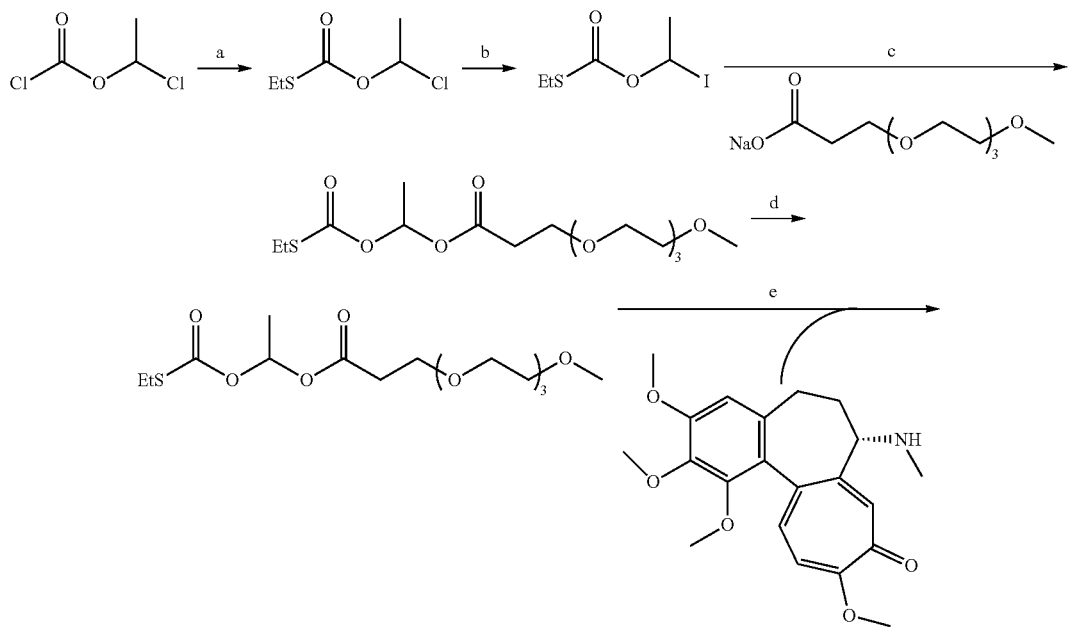

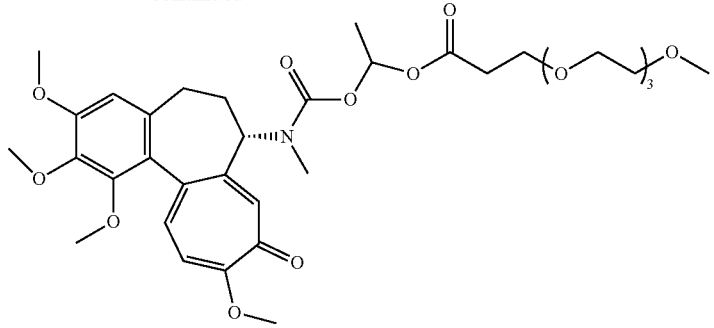

6

Reagents and Conditions: (a) EtSH, Et3N, ether; (b) NaI, acetone; (c) dimethylformamide; (d) SOCl₂; (e) CHCl₃ (Et = ethyl).

Reaction of 1-chloroethyl chloroformate with ethanethiol yields O-(1-chloroethyl)-S-ethylcarbonothioate, which can be converted to the iodo derivative by reaction with sodium iodide. Displacement of iodide from the iodo derivative by the sodium salt of 4,7,10,13-tetraoxatetradecanoic acid yields a carbonothioate, which can react with thionyl chloride to yield the chloroformate. Reaction of the chloroformate with colcemid affords the carbamate prodrug compound 6.

Example 4—In Vitro Microtubule Destabilization in OCY-293 Cells

Prodrug compounds described herein were screened in cell cultures in vitro to determine effectiveness and time-course of microtubule destabilization. Four labile esters of aliphatic acids containing 2, 10 or 16 carbons (compounds 7, 8, and 10), or a branched seven carbon aliphatic chain (compound 9), were employed.

Cell Treatment:

OCY-293 cells stably expressing GFP-tubulin were cultured in 96-well plates at 37° C. in modified DMEM. Cells were treated with colchicine, deacetyl-colchicine or compounds 7, 8, 9, and 10 on a time course for 10, 20, 30, 45, 60, 90, or 120 minutes at 0.3, 1, 3, 10, or 100 µM (see FIGS. 6A-6G, 7A-7G, 8A-8G, 9A-9G, 10A-10G, and 11A-11G). Control cells were treated with vehicle. DAPI was added to each well to identify the nuclei. At each time point, cells were fixed with 4% paraformaldehyde and stored at 4° C. in the dark until imaging.

Imaging and Analysis:

Cells were imaged to assess microtubule structure using fluorescence microscopy (Nikon TIe) with 5 images taken in different locations of each well. The images were digitized in two channels (GFP to visualize tubulin, and therefore microtubules; and DAPI to visualize nuclei). The microtubule area was traced, and nuclei were counted using predictive software (Nikon Elements v4.51) via unbiased automated measurements of each image in each of the wells. The microtubule area was normalized to the number of nuclei.

Figure 7C:
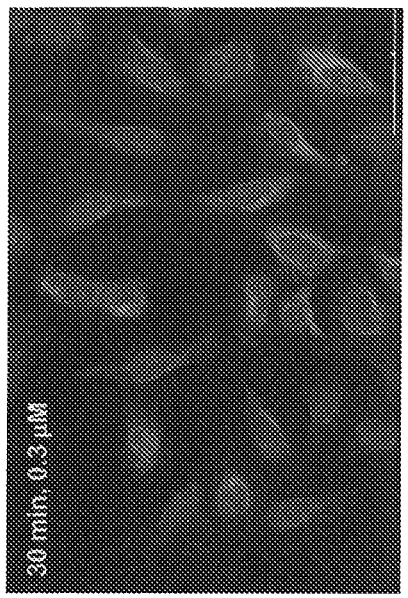
FIGS. 7A-7G illustrate depolymerization studies in OCY-293 cells stably expressing GFP-tubulin upon treatment with deacetyl-colchicine on a time course for 10 minutes, 20 minutes, 30 minutes, 45 minutes, 60 minutes, and 90 minutes, at 0.3 µM, 1 µM, 3 µM, and 10 µM (FIGS. 7A-7F: imaging results for 0.3 µM deacetyl-colchicine at 10 minutes, 20 minutes, 30 minutes, 45 minutes, 60 minutes, and 90 minute.
Figure 7D:
Figure 7A:
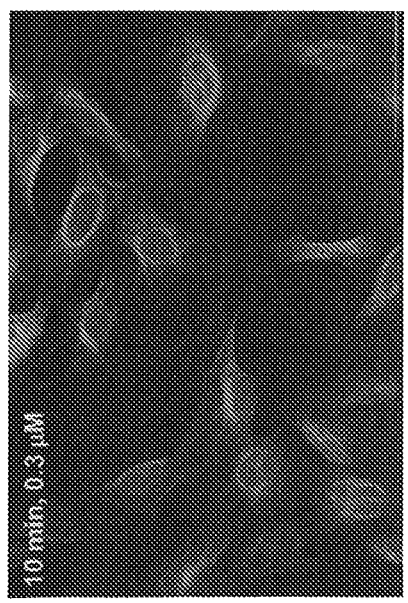
Figure 7B:
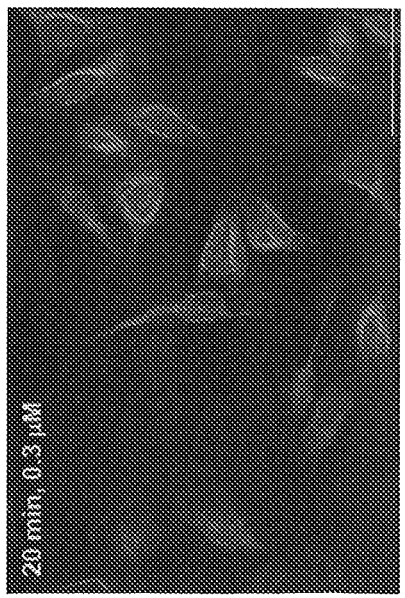
Figure 7G:
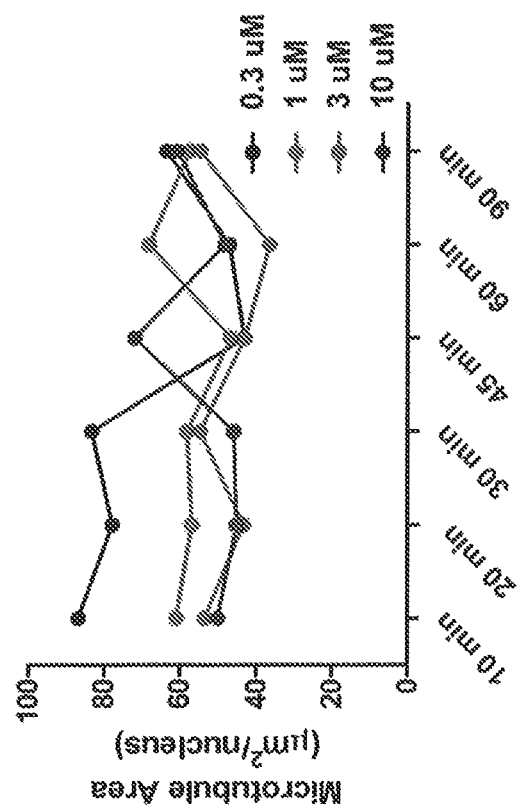
Figure 7E:
Figure 7F:
Figure 8C:
FIGS. 8A-8G illustrate depolymerization studies in OCY-293 cells stably expressing GFP-tubulin upon treatment with compound 7 on a time course for 10 minutes, 20 minutes, 30 minutes, 45 minutes, 60 minutes, 90 minutes, and 120 minutes at 0.3 µM, 1 µM, 10 µM, and 100 µM (FIGS. 8A-8F: imaging results for 0.3 µM compound 7 at 10 minutes, 20 minutes, 30 minutes, 45 minutes, 60 minutes, and 90 minute.
Figure 8D:
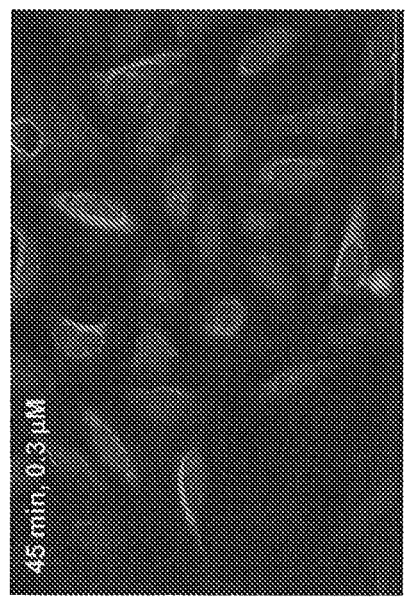
Figure 8A:
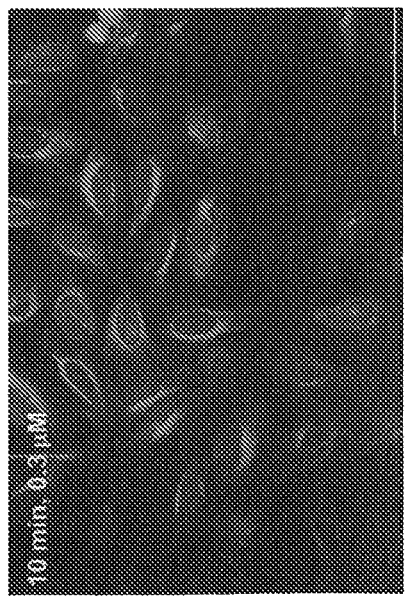
Figure 8B:
Figure 8G:
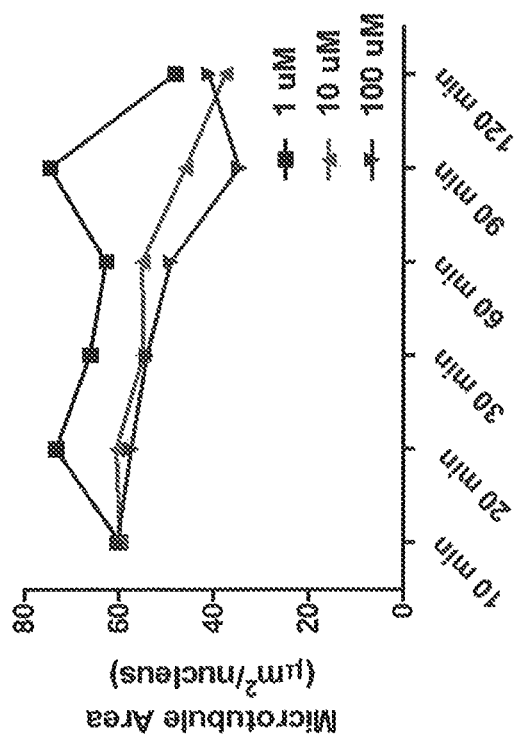
Figure 8E:
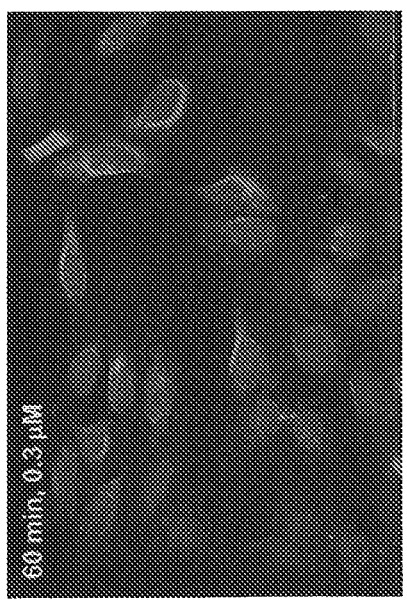
Figure 8F:
Figure 9C:
FIGS. 9A-9G illustrate depolymerization studies in OCY-293 cells stably expressing GFP-tubulin upon treatment with compound 8 on a time course for 10 minutes, 20 minutes, 30 minutes, 60 minutes, 90 minutes, and 120 minutes at 1 µM, 10 µM, and 100 µM (FIGS. 9A-9F: imaging results for 1 µM compound 8 at 10 minutes, 20 minutes, 30 minutes, 60 minutes, 90 minutes, and 120 minute.
Figure 9D:
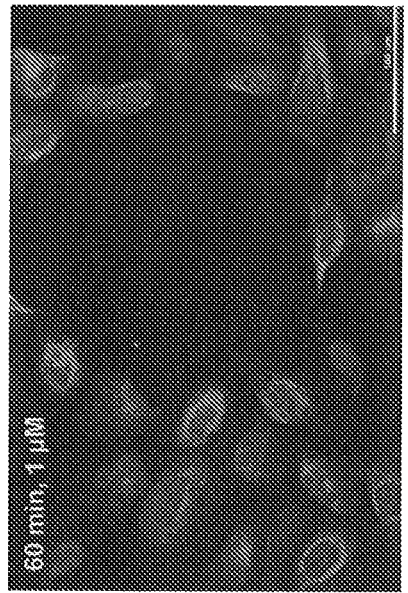
Figure 9A:
Figure 9B:
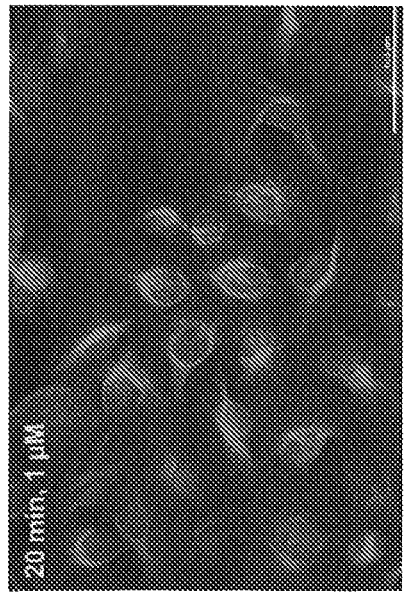
Figure 9G:
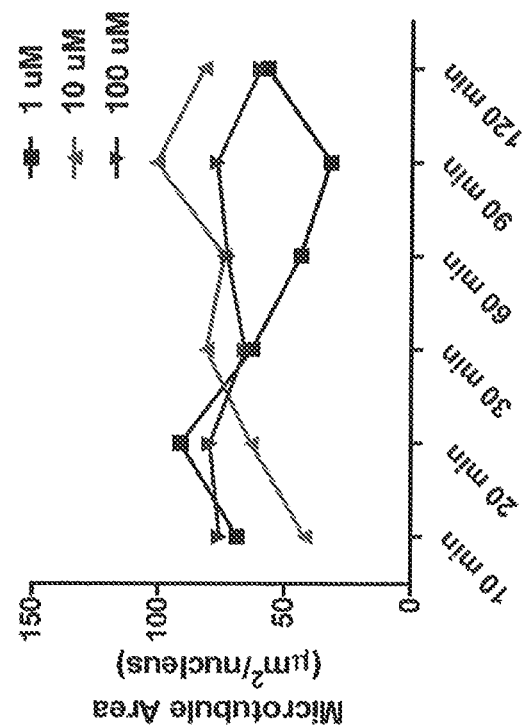
Figure 9E:
Figure 9F:
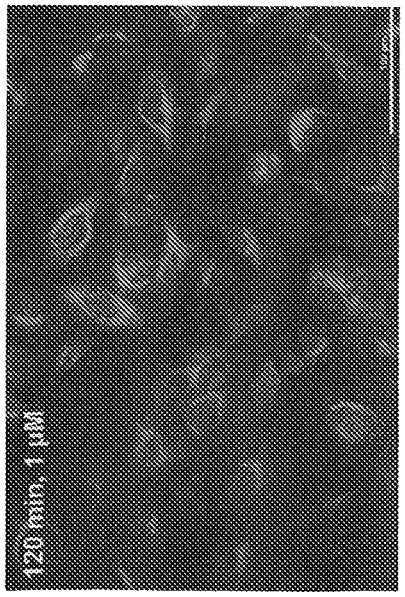
Figure 10C:
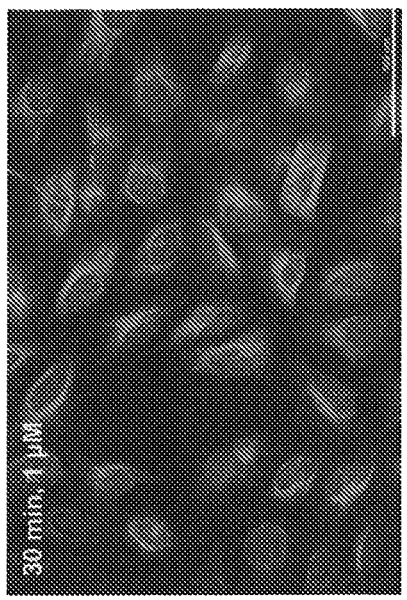
FIGS. 10A-10G illustrate depolymerization studies in OCY-293 cells stably expressing GFP-tubulin upon treatment with compound 9 on a time course for 10 minutes, 20 minutes, 30 minutes, 60 minutes, 90 minutes, and 120 minutes at 1 µM, 10 µM, and 100 µM (FIGS. 10A-10F: imaging results for 1 µM compound 9 at 10 minutes, 20 minutes, 30 minutes, 60 minutes, 90 minutes, and 120 minute.
Figure 10D:
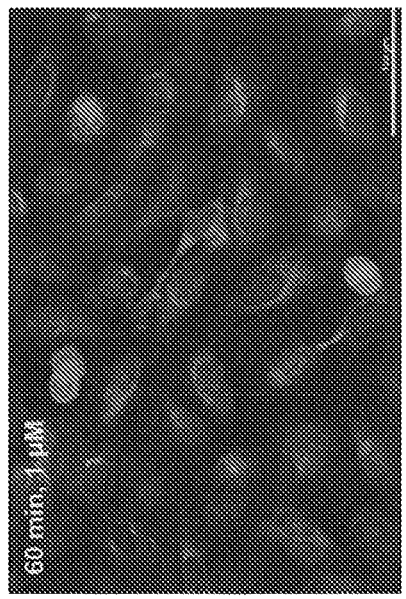
Figure 10A:
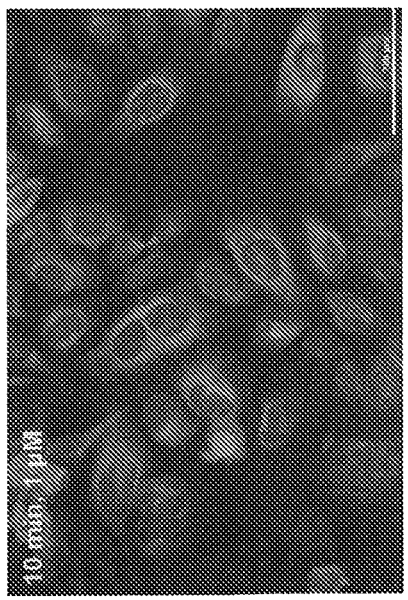
Figure 10B:
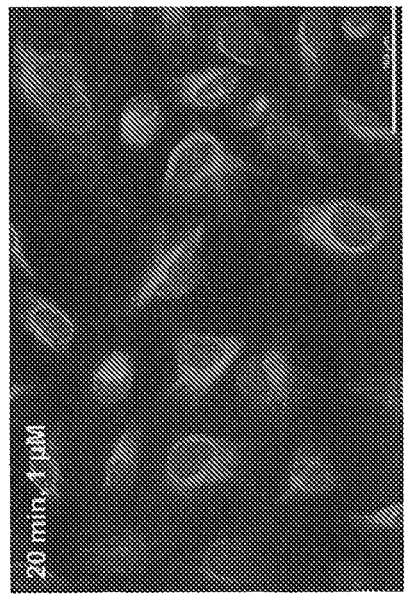
Figure 10G:
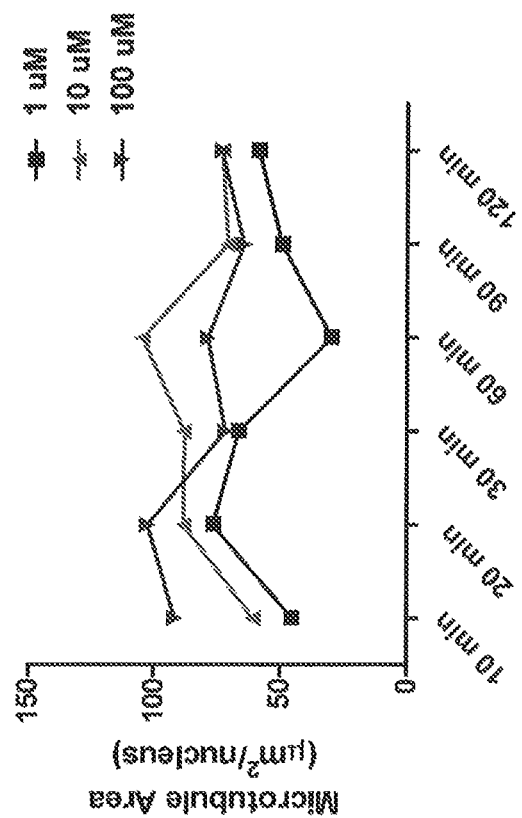
Figure 10E:
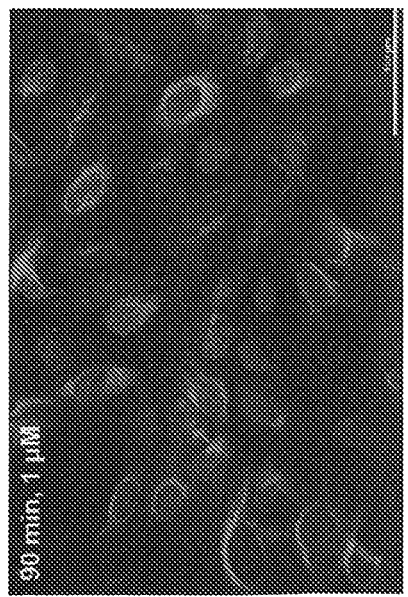
Figure 10F:
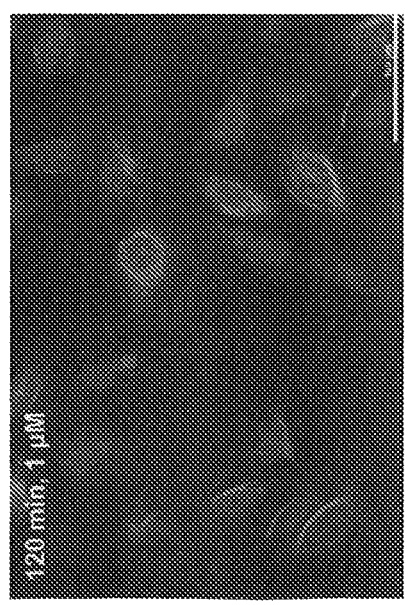
Figure 11A:
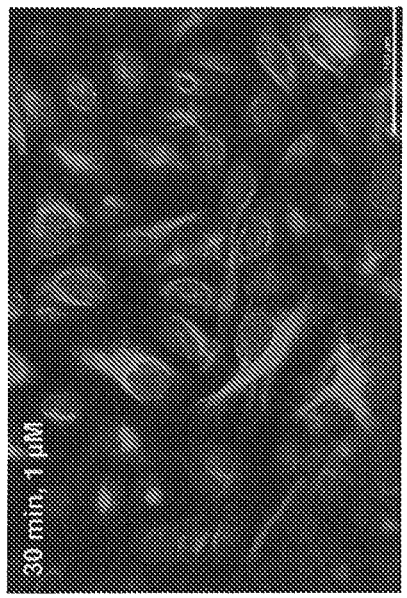
FIGS. 11A-11G illustrate depolymerization studies in OCY-293 cells stably expressing GFP-tubulin upon treatment with compound 10 on a time course for 10 minutes, 20 minutes, 30 minutes, 60 minutes, 90 minutes, and 120 minutes at 1 µM, 10 µM, and 100 µM (FIGS. 11A-11F: imaging results for 1 µM compound 10 at 10 minutes, 20 minutes, 30 minutes, 60 minutes, 90 minutes, and 120 minute.
Figure 11C:
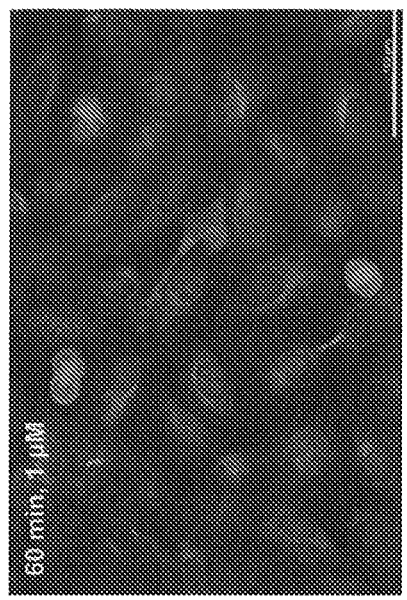
Figure 11B:
Figure 11D:
Figure 11G:
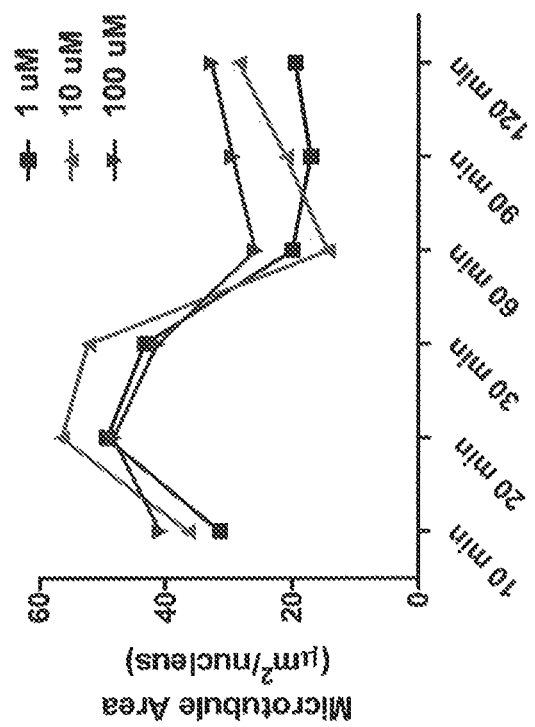
Figure 11E:
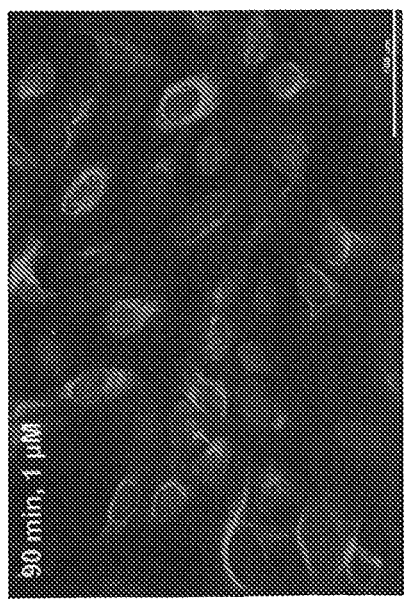
Figure 11F:

Results:

Treatment with either colchicine or deacetyl-colchicine resulted in rapid depolymerization at low concentrations (FIGS. 6A-6G, and 7A-7G). Higher concentrations of deacetyl colchicine resulted in microtubule collapse almost immediately (FIG. 7G). Conversely, treatment with compound 7 resulted in delayed and reduced depolymerization at all concentrations (FIGS. 8A-8G), whereas treatment with compounds 8, 9, and 10 resulted in dampened depolymerization at higher concentrations only compared to deacetyl-colchicine, though their effects on time-course is unclear (FIGS. 9A-9G, 10A-10G, and 11A-11G). Thus, it was demonstrated that labile-esterified colchicinoids dampen and prolong the time-course of action on microtubule depolymerization in an in vitro assay. Without wishing to be bound by any particular theory, it is believed that esterification will also prolong uptake from the bloodstream into the cell, and thus the in vivo effect will be even more pronounced.

REFERENCES

1. Goyenvalle A, Seto J T, Davies K E, Chamberlain J. Therapeutic approaches to muscular dystrophy. Hum Mol Genet [Internet]. 2011/03/26. 2011; 20(R1):R69-78. Available from: http://www.ncbi.nlm.nih.gov/entrez/query.fcgi?cmd=Retrieve&db=PubMed&dopt=Citation&list_uids=21436158 PMID: 21436158
2. Allen D, Whitehead N P, Allen D G, Whitehead N P, Froehner S C. Absence of Dystrophin Disrupts Skeletal Muscle Signaling: Roles of Ca2+, Reactive Oxygen Species, and Nitric Oxide in the Development of Muscular Dystrophy. Physiol Rev. 2015; 96(December):253-305. PMID: 26676145
3. Tidball J G, Wehling-Henricks M. Evolving therapeutic strategies for Duchenne muscular dystrophy: targeting downstream events. Pediatr Res [Internet]. 2004/11/09. 2004; 56(6):831-841. Available from: http://www.ncbi.nlm.nih.gov/entrez/query.fcgi?cmd=Retrieve&db=PubMed&dopt=Citation&list_uids=15531741 PMID: 15531741
4. MD-CARE_Act. Muscular Dystrophy Community Assistance, Research and Education Amendments of 2001 [Internet]. Services D of H and H, editor. MD-CARE Act. National Institutes of Health; 2008. Available from: http://www.cdc.gov/ncbddd/duchenne/documents/MD CARE Act.pdf
5. Khairallah R J, Shi G, Sbrana F, Prosser B L, Borroto C, Mazaitis M J, Hoffman E P, Mahurkar A, Sachs F, Sun Y, Chen Y-WW, Raiteri R, Lederer W J J, Dorsey S G, Ward C W. Microtubules underlie dysfunction in duchenne muscular dystrophy. Sci Signal [Internet]. 2012 Aug. 7 [cited 2013 Aug. 29]; 5(236):ra56. Available from: http://www.pubmedcentral.nih.gov/articlerender.fcgi?artid=3835660&tool=pmcentrez&rendertype=abstract PMID: 22871609

6. Kerr J P, Robison P, Shi G, Bogush A I, Kempema A M, Hexum J K, Becerra N, Harki D a., Martin S S, Raiteri R, Prosser B L, Ward C W. Detyrosinated microtubules modulate mechanotransduction in heart and skeletal muscle. Nat Commun [Internet]. Nature Publishing Group; 2015; 6:8526. Available from: http://www.nature.com/doifinder/10.1038/ncomms9526

7. Khairallah R J, Shi G, Sbrana F, Prosser B L, Borroto C, Mazaitis M J, Hoffman E P, Mahurkar A, Sachs F, Sun Y, Chen Y W, Raiteri R, Lederer W J, Dorsey S G, Ward C W. Microtubules Underlie Dysfunction in Duchenne Muscular Dystrophy. Sci Signal [Internet]. 2012; 5(236): ra56-. Available from: http://stke.sciencemag.org/cgi/content/abstract/sigtrans 8. Khairallah R J, Shi G, Sbrana F, Prosser B L, Borroto C, Mazaitis M J, Hoffman E P, Mahurkar A, Sachs F, Sun Y, Chen Y-WW, Raiteri R, Lederer W J J, Dorsey S G, Ward C W. Microtubules underlie dysfunction in duchenne muscular dystrophy. Sci Signal [Internet]. 2012 Aug. 7 [cited 2013 Aug. 29]; 5(236):ra56. Available from: http://www.pubmedcentral.nih.gov/articlerender.fcgi?artid=3835660&tool=pmcentrez&rende rtype=abstract PMID: 22871609

9. Kendall G C, Mokhonova E I, Moran M, Sejbuk N E, Wang D W, Silva O, Wang R T, Martinez L, Lu Q L, Damoiseaux R, Spencer M J, Nelson S F, Miceli M C. Dantrolene enhances antisense-mediated exon skipping in human and mouse models of Duchenne muscular dystrophy. Sci Transl Med [Internet]. 2012 Dec. 12 [cited 2013 Aug. 29]; 4(164): 164ra160. Available from: http://www.ncbi.nlm.nih.gov/pubmed/23241744 PMID: 23241744

10. Deftereos S, Giannopoulos G, Papoutsidakis N, Panagopoulou V, Kossyvakis C, Raisakis K, Cleman M W, Stefanadis C. Colchicine and the heart: Pushing the envelope. J Am Coll Cardiol [Internet]. Elsevier Inc; 2013; 62(20):1817-1825. Available from: http://dx.doi.org/10.1016/j.jacc.2013.08.726 PMID: 24036026

11. Sozeri B, Kasapcopur O. Biological agents in familial Mediterranean fever focusing on colchicine resistance and amyloidosis. Curr Med Chem [Internet]. 2015 Mar. 11 [cited 2015 Mar. 19]; Available from: http://www.ncbi.nlm.nih.gov/pubmed/25760087 PMID: 25760087

12. Yang L P H. Oral Colchicine (Colcrys Ó) in the Treatment and Prophylaxis of Gout y Profile Report. 2010; 27(10):855-857.

13. Prosser B L, Khairallah R J, Ziman A P, Ward C W, Lederer W J. X-ROS signaling in the heart and skeletal muscle: stretch-dependent local ROS regulates $[Ca^{2+}]i$. J Mol Cell Cardiol [Internet]. Elsevier Ltd; 2013 May [cited 2014 May 1]; 58:172-81. Available from: http://www.ncbi.nlm.nih.gov/pubmed/23220288 PMID: 23220288

14. Niel E, Scherrmann J. Colchicine today. 2006; 73:672-678.

15. Cocco G, Chu D C C, Pandolfi S. Colchicine in clinical medicine. A guide for intemists. Eur J Intern Med. 2010; 21(6):503-508. PMID: 21111934

16. Press D. Eteplirsen in the treatment of Duchenne muscular dystrophy. 2017; 533-545.

17. Global Data. GlobalData Report—OpportunityAnalyzer: Duchenne Muscular Dystrophy—Opportunity and Market Analysis to 2019 [Internet]. 2016. Available from: https://www.globaldata.com/store/report/gdhc038poa-opportunityanalyzer/

18. Dorsey S G, Lovering R M, Renn C L, Leitch C C, Liu X, Tallon L J, Sadzewicz L D, Pratap A, Ott S, Sengamalay N, Jones K M, Barrick C, Fulgenzi G, Becker J, Voelker K, Talmadge R, Harvey B K, Wyatt R M, Vemon-Pitts E, Zhang C, Shokat K, Fraser-Liggett C, Balice-Gordon R J, Tessarollo L, Ward C W. Genetic deletion of trkB.T1 increases neuromuscular function. Am J Physiol Cell Physiol [Internet]. 2012 Jan. 1 [cited 2013 May 2]; 302(1):C141-53. Available from: http://www.pubmedcentral.nih.gov/articlerender.fcgi?artid=3328911 &tool=pmcentrez&rende rtype=abstract PMID: 21865582

19. Cohn R D, van Erp C, Habashi J P, Soleimani A A, Klein E C, Lisi M T, Gamradt M, ap Rhys C M, Holm T M, Loeys B L, Ramirez F, Judge D P, Ward C W, Dietz H C. Angiotensin I I type 1 receptor blockade attenuates TGF-beta-induced failure of muscle regeneration in multiple myopathic states. Nat Med [Internet]. 2007 February [cited 2014 Feb. 5]; 13(2):204-10. Available from: http://www.ncbi.nlm.nih.gov/entrez/query.fcgi?cmd=Retrieve&db=PubMed&dopt=Citation &list_uids=17237794 PMID: 17237794

20. Lovering R M, Michaelson L, Ward C W. Malformed mdx myofibers have normal cytoskeletal architecture yet altered EC coupling and stress-induced Ca2+ signaling. Am J Physiol Cell Physiol [Internet]. American Physiological Society; 2009 Sep. 1 [cited 2014 Feb. 5]; 297(3):C571-80. Available from: http://www.pubmedcentral.nih.gov/articlerender.fcgi?artid=2740390&tool=pmcentrez&rende rtype=abstract PMID: 19605736

21. Pratt S J, Lawlor M W, Shah S B, Lovering R M. An in vivo rodent model of contraction-induced injury in the quadriceps muscle. Injury. 2012; 43(6):788-793. PMID: 22001505

22. Pratt S J, Shah S B, Ward C W, Inacio M P, Stains J P, Lovering R M. Effects of in vivo injury on the neuromuscular junction in healthy and dystrophic muscles. J Physiol. 2013; 591:559-570. PMID: 23109110

23. Pratt S J P, Lovering R M. A stepwise procedure to test contractility and susceptibility to injury for the rodent quadriceps muscle. J Biol Methods [Internet]. 2014 Oct. 28 [cited 2014 Nov. 6]; 1(2):8. Available from: http://www.jbmethods.org/jbm/article/view/34

24. Lovering R M, De Deyne P G. Contractile function, sarcolemma integrity, and the loss of dystrophin after skeletal muscle eccentric contraction-induced injury. Am J Physiol Cell Physiol [Internet]. 2003/10/03. 2004 February [cited 2014 Feb. 7]; 286(2):C230-8. Available from: http://www.ncbi.nlm.nih.gov/entrez/query.fcgi?cmd=Retrieve&db=PubMed&dopt=Citation &list_uids=14522817 PMID: 14522817

25. Bellinger A M, Reiken S, Dura M, Murphy P W, Deng S X, Landry D W, Nieman D, Lehnart S E, Samaru M, LaCampagne A, Marks A R. Remodeling of ryanodine receptor complex causes "leaky" channels: a molecular mechanism for decreased exercise capacity. Proc Natl Acad Sci USA [Internet]. 2008/02/13. 2008; 105(6):2198-2202. Available from: http://www.ncbi.nlm.nih.gov/entrez/query.fcgi?cmd=Retrieve&db=PubMed&dopt=Citation &list_uids=18268335 PMID: 18268335

26. Ferron G M, Rochdi M, Jusko W J, Scherrmann J M Oral ansorption characteristics and pharmacokinetics of colchicine in healthy volenteers after single and multiple doses. J Clin Pharmacol 1996; 36: 874-883.

It is claimed:

1. A prodrug of formula:

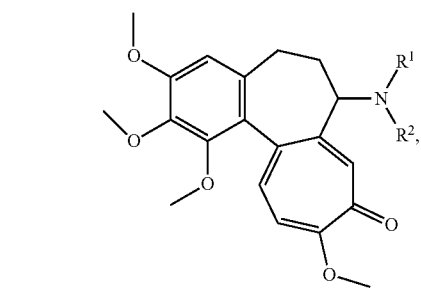
(I)

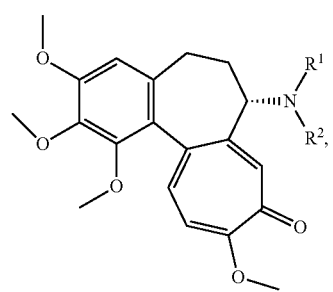
(II)

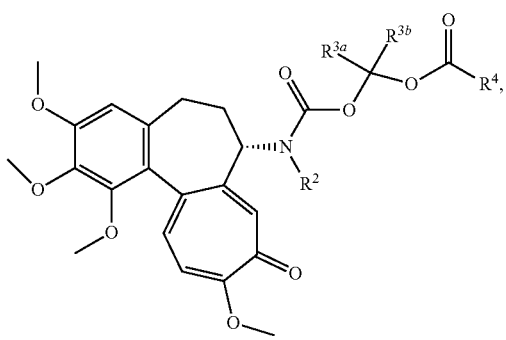
(III)

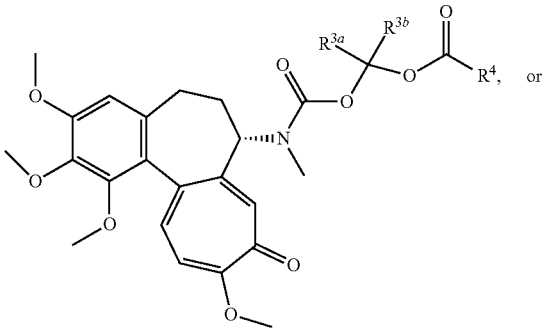
(IV)

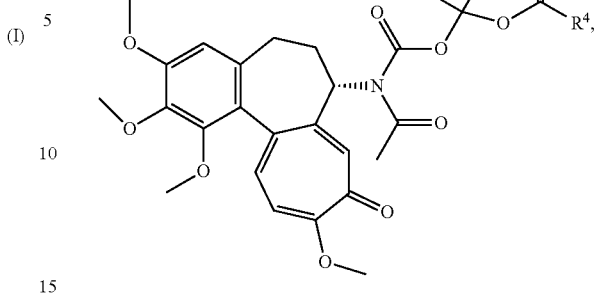
(V)

wherein $R^1$ is a substituent selected from the group consisting of carboxyl and —C(=O)O-alkyl-OC(=O)-alkyl;

$R^2$ is a substituent selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

$R^{3a}$ and $R^{3b}$ are substituents independently selected from the group consisting of H, and optionally substituted alkyl, alkylaryl, alkylhetaryl, alkylheterocycloalkyl, alkenyl, alkenyl-cycloalkyl, alkynyl, alkynyl-cycloalkyl, cycloalkyl, cycloalkyl-alkenyl, cycloalkyl-heterocycloalkyl, cycloalkyl-heteroaryl, aryl, heteroaryl, acyloxy, acyl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroarylalkyl, heterocycloalkyl, and heterocycloalkyl;

$R^4$ is a substituent selected from the group consisting of H, and optionally substituted alkyl, alkoxy, -(alkoxy)$_n$-alkyl, heteroalkyl, and -(alkyl)$_n$-alkyl; n is an integer of 1-250; and the pharmaceutically acceptable salts thereof.

2. The prodrug of claim 1, wherein $R^1$ is optionally substituted —C(=O)O-alkyl-OC(=O)-alkyl.

3. The prodrug of claim 1, wherein $R^2$ is a substituent selected from the group consisting of H, and optionally substituted alkyl, aryl, ester, heteroaryl, and acyl.

4. The prodrug of claim 1, wherein $R^{3a}$ and $R^{3b}$ are substituents independently selected from the group consisting of H, and optionally substituted alkyl, aryl, and heteroaryl.

5. The prodrug of claim 1, wherein $R^4$ is a substituent selected from the group consisting of H, —CH$_3$, and optionally substituted —(CH$_2$)$_n$-alkyl, —(CH$_2$CH$_2$O)$_n$-alkyl, -(alkyl)$_n$-CH$_3$, and -(alkoxy)$_n$-CH$_3$, wherein n is an integer of 1-250.

6. The prodrug of claim 1, wherein n is an integer of 1 to 10, or 10 to 20, or 20 to 30, or 30 to 40, or 40 to 50, or 50 to 60, or 60 to 70, or 70 to 80, or 80 to 90, or 90 to 100, or 100 to 110, or 110 to 120, or 120 to 130, or 130 to 140, or 140 to 150, or 150 to 160, or 160 to 170, or 170 to 180, or 180 to 190, or 190 to 200, or 200 to 210, or 210 to 220, or 220 to 230, or 230 to 240, or 240 to 250.

7. The prodrug of claim 1, wherein the prodrug is:
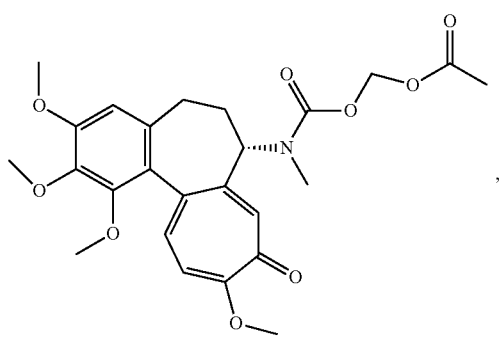
1
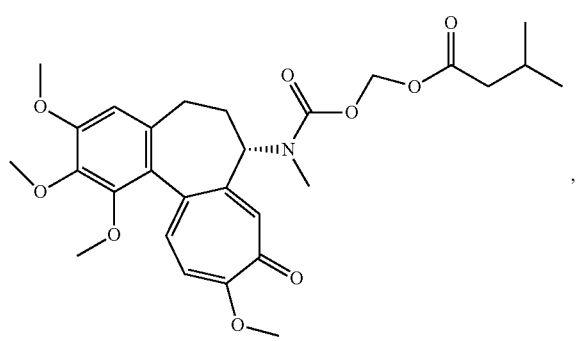
2
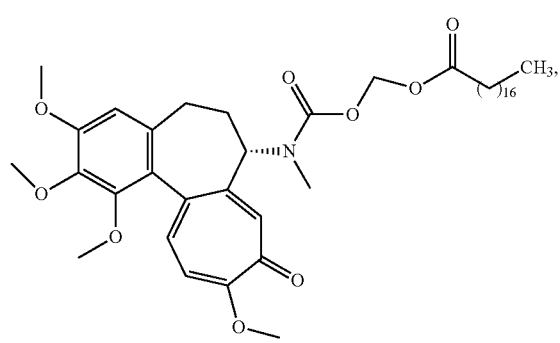
3
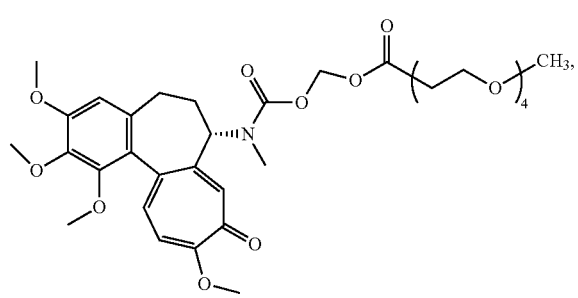
4
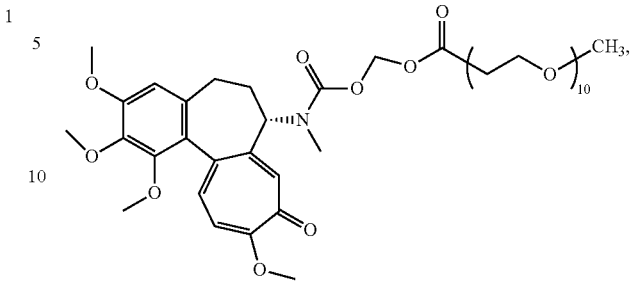
5
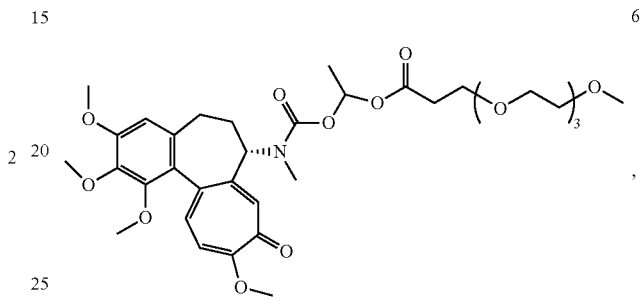
6
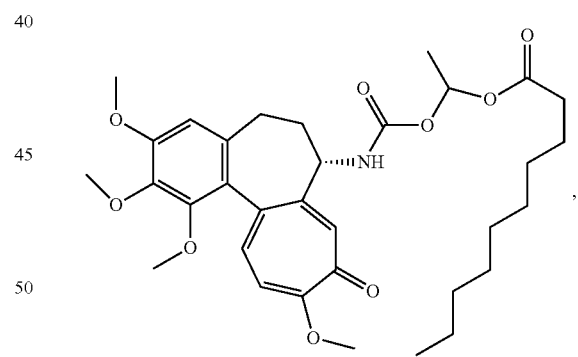
7
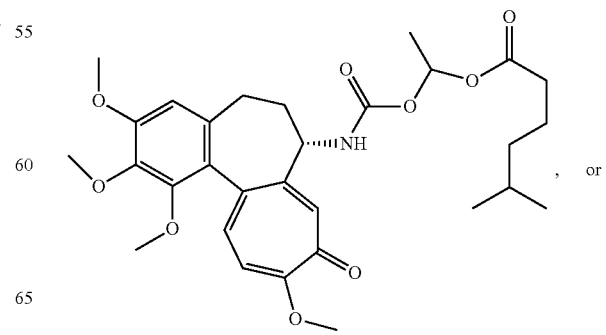
8
9
, or

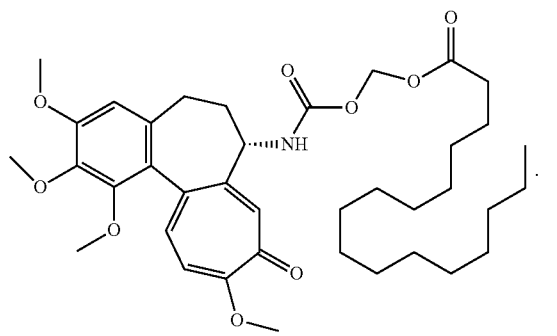
8. The prodrug of claim 1, wherein the active-metabolite of the prodrug is colchicine, de-acetyl colchicine, or colcemid.
9. The prodrug of claim 1, wherein the active-metabolite of the prodrug inhibits microtubule polymerization.
* * * * *